United States Patent
Xu et al.

(10) Patent No.: US 10,702,473 B2
(45) Date of Patent: Jul. 7, 2020

(54) LIPOSOME FORMULATION FOR DELIVERY OF WNT SIGNAL PATHWAY INHIBITOR

(71) Applicant: Curegenix, Inc., Guangzhou (CN)

(72) Inventors: Yuhong Xu, Guangzhou (CN); Meiqing Tu, Guangzhou (CN); Xiaojing Chen, Guangzhou (CN)

(73) Assignee: Curegenix, Inc., Guangzhou (CN)

(*) Notice: Subject to any disclaimer, the term of this patent is extended or adjusted under 35 U.S.C. 154(b) by 0 days.

(21) Appl. No.: 15/944,581

(22) Filed: Apr. 3, 2018

(65) Prior Publication Data
US 2019/0022003 A1  Jan. 24, 2019

(30) Foreign Application Priority Data
Jul. 21, 2017  (CN) .......................... 2017 1 0600514

(51) Int. Cl.
*A61K 9/127* (2006.01)
*A61K 31/444* (2006.01)
(Continued)

(52) U.S. Cl.
CPC ............ *A61K 9/127* (2013.01); *A61K 9/1271* (2013.01); *A61K 31/444* (2013.01); *A61K 31/4725* (2013.01); *A61K 31/496* (2013.01); *A61K 31/497* (2013.01); *A61K 31/4985* (2013.01); *A61K 31/501* (2013.01);
(Continued)

(58) Field of Classification Search
CPC .... A61K 9/127; A61K 9/1271; A61K 31/506; A61K 31/5377; A61K 31/497; A61K 31/501; A61K 31/541; A61K 31/4985; A61K 31/4725; A61K 31/444; A61K 31/496; A61K 9/1278; A61K 9/0019; A61K 45/00; A61K 47/24
See application file for complete search history.

(56) References Cited

U.S. PATENT DOCUMENTS 9,556,144 B2  1/2017  An
9,713,612 B2  7/2017  An
(Continued)

FOREIGN PATENT DOCUMENTS

CN  102558173  *  7/2012
CN  102558173 B  5/2015
(Continued)

OTHER PUBLICATIONS

Seguin. J., et al in International Journal of Pharmaceutics, vol. 444, issues 1-2, Feb. 2013, pp. 146-154.*

*Primary Examiner* — Gollamudi S Kishore
(74) *Attorney, Agent, or Firm* — K&L Gates LLP; Louis C. Cullman; David Diamond

(57) ABSTRACT

A liposome formulation for delivery of Wnt signal pathway inhibitor is provided herein, which comprises lipid molecules and Wnt signal pathway inhibitor, wherein the liposome formulation is prepared through following steps: (1) providing an aqueous solution of the Wnt signal pathway inhibitor and providing an alcoholic solution of the lipid molecules, (2) mixing the aqueous solution of the Wnt signal pathway inhibitor and the alcoholic solution of the lipid molecules, (3) removing alcohol solvent to obtain the liposome formulation with Wnt signal pathway inhibitor encapsulated therein.

7 Claims, 2 Drawing Sheets

LIPOSOME FORMULATION FOR DELIVERY OF WNT SIGNAL PATHWAY INHIBITOR

(51) Int. Cl.
  *A61K 31/4725* (2006.01)
  *A61K 31/4985* (2006.01)
  *A61K 31/496* (2006.01)
  *A61K 31/541* (2006.01)
  *A61K 31/501* (2006.01)
  *A61K 31/497* (2006.01)
  *A61K 31/5377* (2006.01)
  *A61K 31/506* (2006.01)

(52) U.S. Cl.
  CPC ........ *A61K 31/506* (2013.01); *A61K 31/5377* (2013.01); *A61K 31/541* (2013.01); *A61K 9/1278* (2013.01)

(56) References Cited

U.S. PATENT DOCUMENTS

| | | |
|---|---|---|
| 9,744,169 B2 | 8/2017 | An |
| 10,087,181 B2 | 10/2018 | An |
| 10,238,652 B2 | 3/2019 | An |
| 10,285,988 B2 | 5/2019 | An |
| 2008/0241161 A1* | 10/2008 | Hosokawa ......... C07K 16/3015 424/142.1 |
| 2009/0004185 A1 | 1/2009 | Venkatesan et al. |
| 2009/0069338 A1 | 3/2009 | Dickson, Jr. et al. |
| 2011/0237573 A1 | 9/2011 | Cheng et al. |
| 2012/0196916 A1 | 8/2012 | deLong et al. |
| 2012/0270858 A1 | 10/2012 | Tao et al. |
| 2015/0132301 A1* | 5/2015 | Hoey ................. A61K 39/3955 424/134.1 |
| 2015/0157633 A1* | 6/2015 | Lum ...................... A61K 45/06 514/255.01 |
| 2016/0130222 A1* | 5/2016 | Faloon ................. C07D 333/34 514/395 |
| 2018/0112273 A1 | 4/2018 | Qin et al. |
| 2018/0153884 A1 | 6/2018 | Qin et al. |
| 2019/0022002 A1 | 1/2019 | Xu et al. |
| 2019/0142827 A1 | 5/2019 | An |
| 2019/0209558 A1 | 7/2019 | An |

FOREIGN PATENT DOCUMENTS

| | | |
|---|---|---|
| WO | 2006/074428 A2 | 7/2006 |
| WO | 2013/185353 A1 | 12/2013 |

* cited by examiner

LIPOSOME FORMULATION FOR DELIVERY OF WNT SIGNAL PATHWAY INHIBITOR

LIPOSOME FORMULATION FOR DELIVERY OF WNT SIGNAL PATHWAY INHIBITOR

CROSS REFERENCE TO RELATED APPLICATION

This application claims the benefit of, and priority to Chinese Application No.: 201710600514.4, filed on Jul. 21, 2017, the entire disclosure of which is hereby incorporated by reference in its entirety.

FIELD OF THE INVENTION

The present invention relates to a liposome formulation for delivery of a Wnt signal pathway inhibitor and methods for preparing the same.

BACKGROUND

A liposome is a microvesicle with a lipid bilayer which resembles the structure of a cell membrane, with a variety of advantages such as excellent biocompatibility, targeting ability, capability of increasing effective concentration of pharmaceuticals, and reducing toxicity of pharmaceuticals and the like. Depending on the mechanism for loading pharmaceuticals into the liposome, there are active and passive loading methods. The passive loading method is commonly used in the art. Such method is suitable for loading pharmaceuticals with excellent lipid solubility or water solubility. However, this passive loading method has low encapsulation efficacy and has limitations due to lipid solubility or water solubility of pharmaceuticals.

The Wnt signal pathway involves a variety of complicated biochemical reactions, and plays a key role in regulation of embryonic development. Dysfunction of the Wnt pathway has close correlation with tumorigenesis. Recently, the relation between the Wnt signal pathway and human tumors has attracted increasing attention and has become a worldwide hot research topic. It has been shown that Wnt signal pathway inhibitors can be widely used in the treatment of tumors. However, further clinical investigation of Wnt signal pathway inhibitors as novel pharmaceuticals is hindered due to the toxicity of Wnt signal pathway inhibitors. Liposomes can be used as a superior delivery vehicle for pharmaceuticals and exhibit excellent biocompatibility. Therefore, liposomes can be used as a delivery vehicle for Wnt signal pathway inhibitors, in which a therapeutically effective amount of a Wnt signal pathway inhibitor is encapsulated, and such liposomes will be widely used in treatment of tumors.

SUMMARY

In one aspect, embodiments of the present invention provide a liposome formulation for delivery of a Wnt signal pathway inhibitor, comprising lipid molecules and a Wnt signal pathway inhibitor, wherein the liposome formulation is prepared through following steps: (1) providing an aqueous solution of the Wnt signal pathway inhibitor and an alcoholic solution of the lipid molecules; (2) mixing the aqueous solution of the Wnt signal pathway inhibitor and the alcoholic solution of the lipid molecules; and (3) removing the alcohol solvent to obtain the liposome formulation with a Wnt signal pathway inhibitor encapsulated therein.

In some embodiments, before mixing the aqueous solution of the Wnt signal pathway inhibitor and the alcoholic solution of the lipid molecules, an ammonium salt solution is added to the alcoholic solution of the lipid molecules to form blank vesicles and then the blank vesicles are subjected to dialysis using the ammonium salt solution, to form a concentration gradient from interior to exterior of the blank vesicles. And, prior to mixing the aqueous solution of the Wnt signal pathway inhibitor and the alcoholic solution of the lipid molecules, a solubilizing agent is added to the aqueous solution of the Wnt signal pathway inhibitor and then the blank vesicles upon dialysis are mixed with the aqueous solution of the Wnt signal pathway inhibitor containing the solubilizing agent, thereby loading the Wnt signal pathway inhibitor into the blank vesicles by virtue of concentration gradient from interior to exterior of the blank vesicles. The resultant liposome formulation encapsulates the Wnt signal pathway inhibitor to have a concentration higher than 0.5 mg/ml. The ammonium salt solution may be ammonium sulfate solution. The solubilizing agent may be β-cyclodextrin.

The Wnt signal pathway inhibitor within the liposome formulation as provided herein is selected from the compounds having the following Formula I:

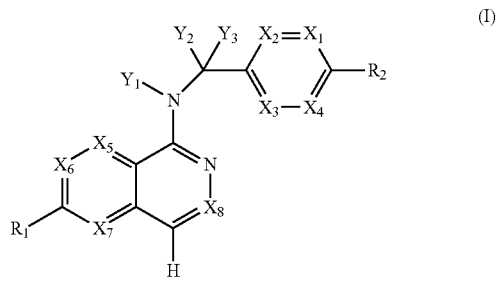

or a pharmaceutically acceptable salt thereof, wherein $X_1$, $X_2$, $X_3$ and $X_4$ are independently $CR_4$ or N;

$Y_1$, $Y_2$, and $Y_3$ are independently hydrogen, $R_1$ is

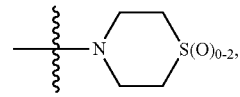

aryl, morpholinyl, piperazinyl, or 6 membered heteroaryl ring containing 1-2 heteroatoms selected from N, O and S, each of which can be optionally substituted with $R_4$;

$R_2$ is

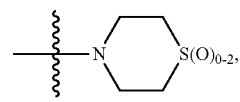

aryl, morpholinyl, piperazinyl, or 6 membered heteroaryl ring containing 1-2 heteroatoms selected from N, O and S, each of which can be optionally substituted with $R_4$;

$R_4$ is hydrogen, halo, $C_{1-6}$alkoxyl, $C_{1-6}$alkyl, each of which can be optionally substituted with halo, hydroxyl, alkoxyl and cyano;

the 6 membered heteroaryl ring is selected from:

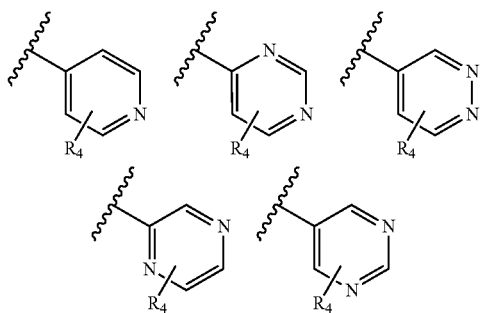

and wherein the Formula I has the following core structure:

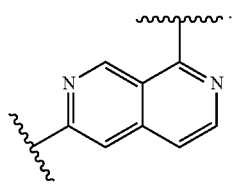 [SMILES: *c1cc2ccnc(*)c2cn1]

The Wnt signal pathway inhibitor within the liposome formulation as provided herein is selected from the compounds having the following Formula II:

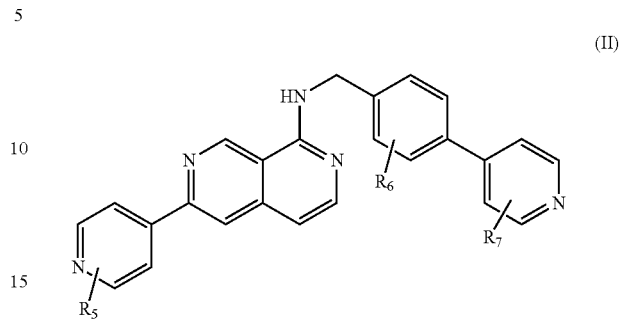

(II)

or a pharmaceutically acceptable salt thereof, wherein $R_5$, $R_6$ and $R_7$ are independently selected from the group consisting of hydrogen, halo, $C_{1-6}$alkoxyl, $C_{1-6}$alkyl, wherein, each of $C_{1-6}$alkoxyl and $C_{1-6}$alkyl can be optionally substituted with halo, hydroxyl, alkoxyl or cyano.

In some embodiments, the Wnt signal pathway inhibitor within the liposome formulation as provided herein is the compound selected from the below table or the pharmaceutically acceptable salt thereof.

TABLE 1

| Compound | Structure |
|---|---|
| 1 | 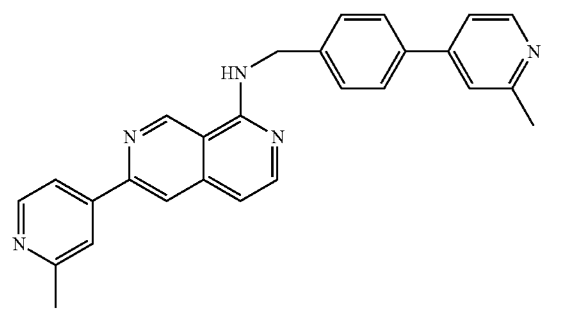 [SMILES: Cc1cc(-c2ccc(CNc3nccc4cc(-c5ccnc(C)c5)ncc34)cc2)ccn1] |
| 2 | 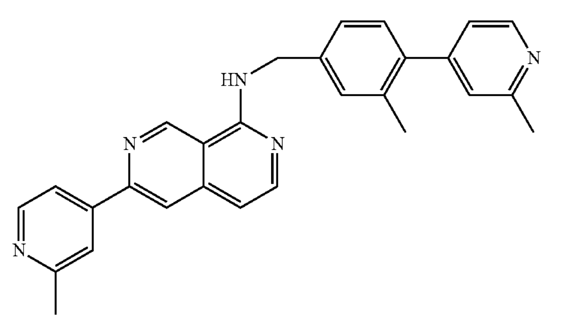 [SMILES: Cc1cc(-c2cc3ccnc(NCc4ccc(-c5ccnc(C)c5)c(C)c4)c3cn2)ccn1] |

TABLE 1-continued
| Compound | Structure |
| --- | --- |
| 3 | 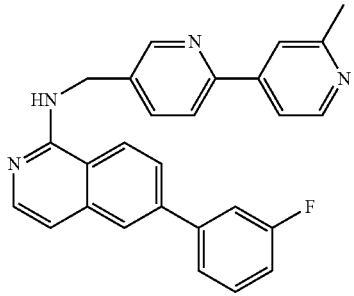 [SMILES: Cc1cc(-c2ccc(CNc3nccc4cc(-c5cccc(F)c5)ccc34)cn2)ccn1] |
| 4 | 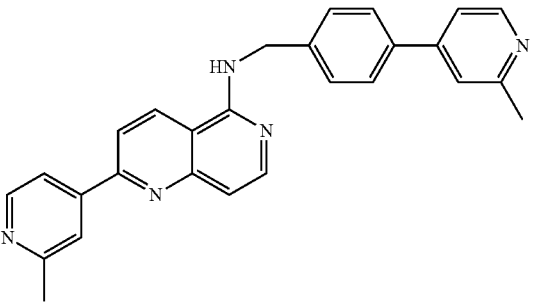 |
| 5 | 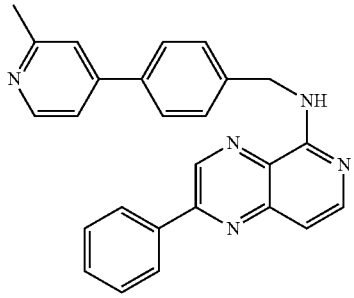 [SMILES: Cc1cc(-c2ccc(CNc3nccc4nc(-c5ccccc5)cnc34)cc2)ccn1] |
| 6 | 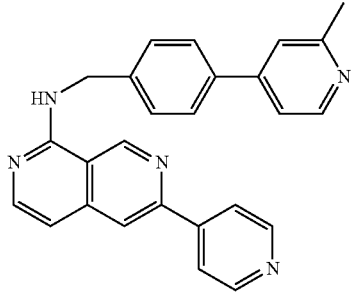 |
| 7 | 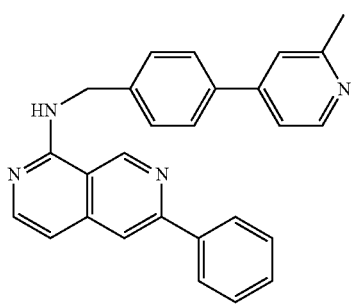 [SMILES: Cc1cc(-c2ccc(CNc3nccc4cc(-c5ccccc5)ncc34)cc2)ccn1] |

TABLE 1-continued

| Compound | Structure |
|---|---|
| 8 | 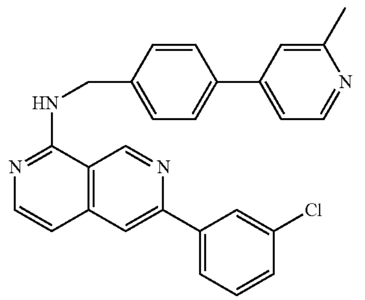 [SMILES: Cc1cc(-c2ccc(CNc3nccc4cc(-c5cccc(Cl)c5)ncc34)cc2)ccn1] |
| 9 | 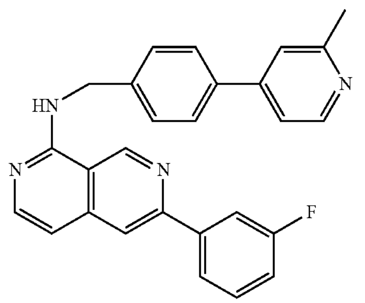 |
| 10 | 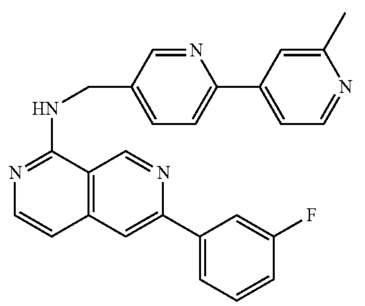 [SMILES: Cc1cc(-c2ccc(CNc3nccc4cc(-c5cccc(F)c5)ncc34)cn2)ccn1] |
| 11 | 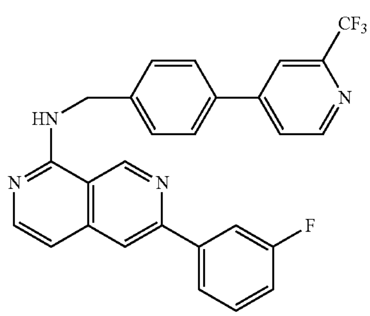 [SMILES: Fc1cccc(-c2cc3ccnc(NCc4ccc(-c5ccnc(C(F)(F)F)c5)cc4)c3cn2)c1] |
| 12 | 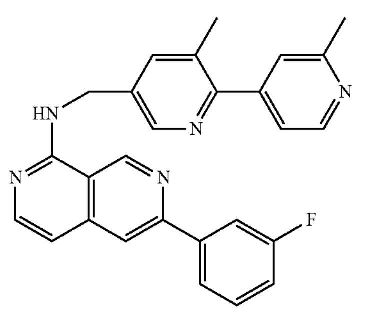 [SMILES: Cc1cc(-c2ncc(CNc3nccc4cc(-c5cccc(F)c5)ncc34)cc2C)ccn1] |

TABLE 1-continued

| Compound | Structure |
|---|---|
| 13 | 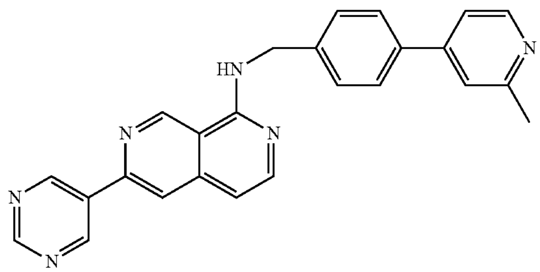 [SMILES: Cc1cc(-c2ccc(CNc3nccc4cc(-c5cncnc5)ncc34)cc2)ccn1] |
| 14 | 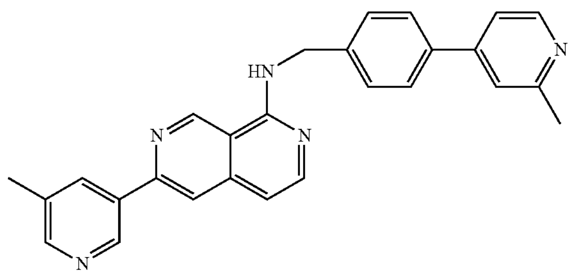 |
| 15 | 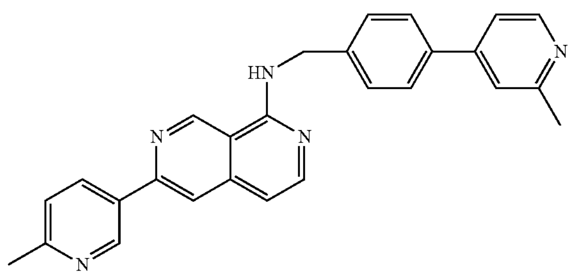 |
| 16 | 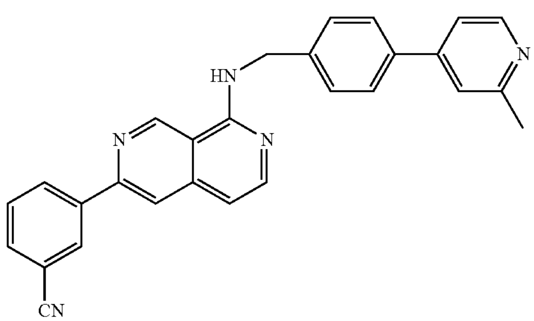 [SMILES: Cc1cc(-c2ccc(CNc3nccc4cc(-c5cccc(C#N)c5)ncc34)cc2)ccn1] |
| 17 | 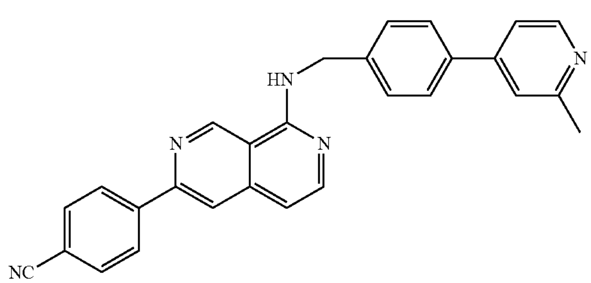 [SMILES: Cc1cc(-c2ccc(CNc3nccc4cc(-c5ccc(C#N)cc5)ncc34)cc2)ccn1] |

TABLE 1-continued

| Compound | Structure |
|---|---|
| 18 | 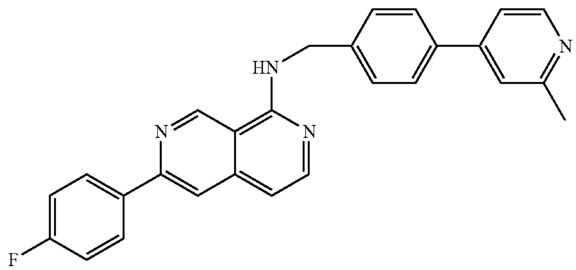 [SMILES: Cc1cc(-c2ccc(CNc3nccc4cc(-c5ccc(F)cc5)ncc34)cc2)ccn1] |
| 19 | 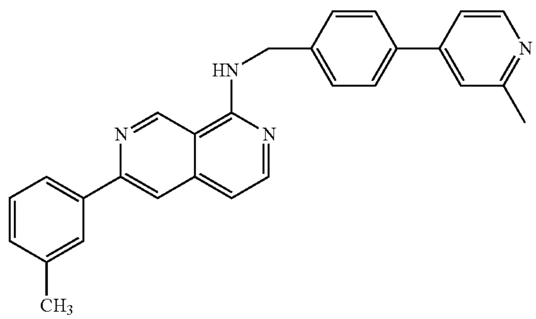 [SMILES: Cc1cccc(-c2cc3ccnc(NCc4ccc(-c5ccnc(C)c5)cc4)c3cn2)c1] |
| 20 | 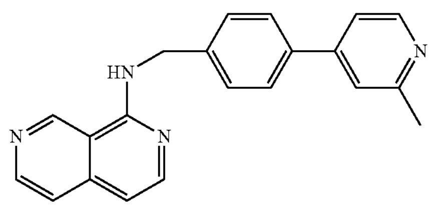 [SMILES: Cc1cc(-c2ccc(CNc3nccc4ccncc34)cc2)ccn1] |
| 21 | 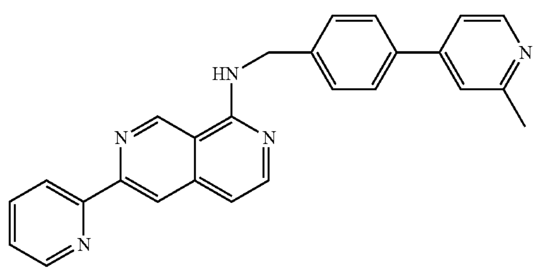 [SMILES: Cc1cc(-c2ccc(CNc3nccc4cc(-c5ccccn5)ncc34)cc2)ccn1] |
| 22 | 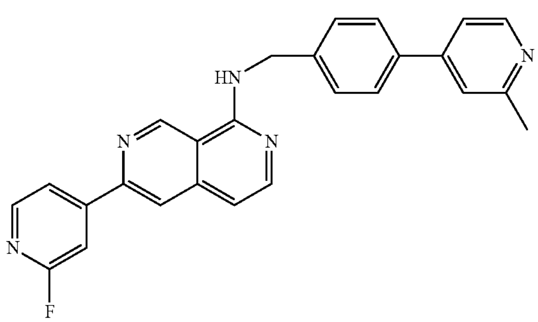 [SMILES: Cc1cc(-c2ccc(CNc3nccc4cc(-c5ccnc(F)c5)ncc34)cc2)ccn1] |

TABLE 1-continued

| Compound | Structure |
|---|---|
| 23 | 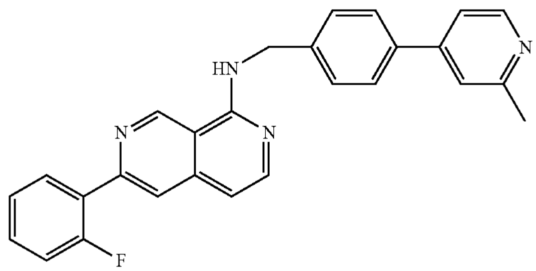 [SMILES: Cc1cc(-c2ccc(CNc3nccc4cc(-c5ccccc5F)ncc34)cc2)ccn1] |
| 24 | 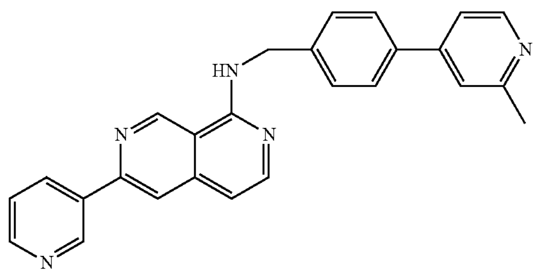 [SMILES: Cc1cc(-c2ccc(CNc3nccc4cc(-c5cccnc5)ncc34)cc2)ccn1] |
| 25 | 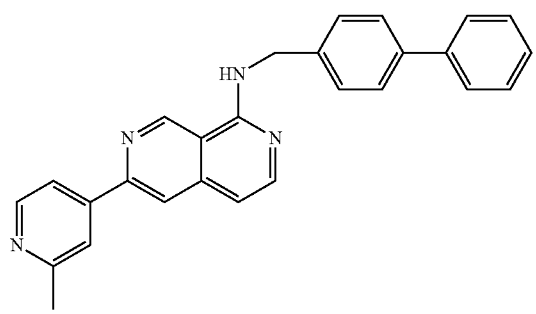 |
| 26 | 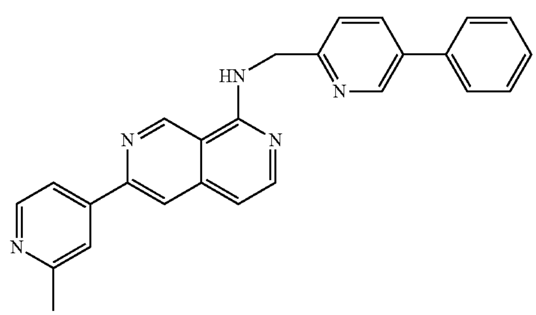 [SMILES: Cc1cc(-c2cc3ccnc(NCc4ccc(-c5ccccc5)cn4)c3cn2)ccn1] |
| 27 | 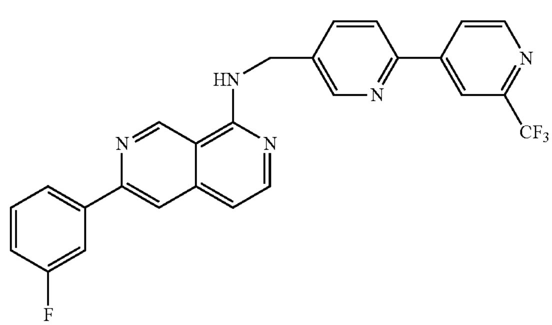 [SMILES: Fc1cccc(-c2cc3ccnc(NCc4ccc(-c5ccnc(C(F)(F)F)c5)nc4)c3cn2)c1] |

TABLE 1-continued

| Compound | Structure |
|----------|-----------|
| 28 | 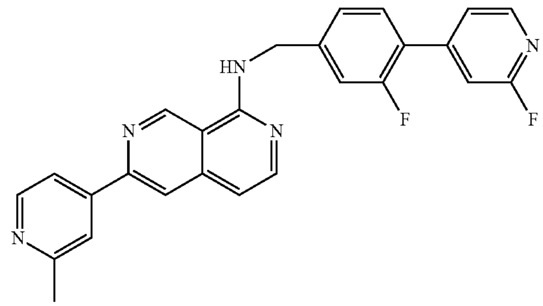 [SMILES: Cc1cc(-c2cc3ccnc(NCc4ccc(-c5ccnc(F)c5)c(F)c4)c3cn2)ccn1] |
| 29 | 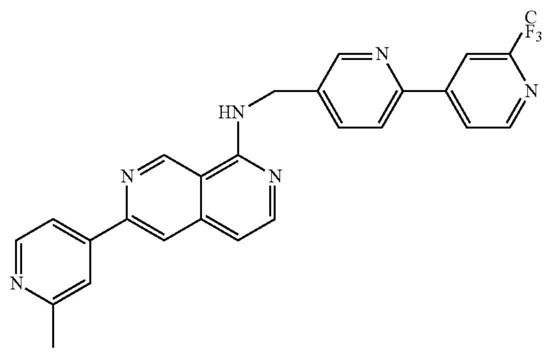 [SMILES: Cc1cc(-c2cc3ccnc(NCc4ccc(-c5ccnc(C(F)(F)F)c5)nc4)c3cn2)ccn1] |
| 30 | 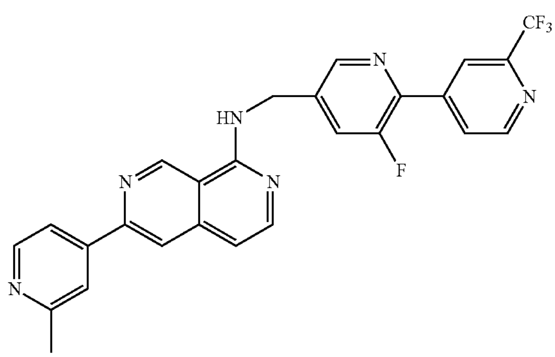 [SMILES: Cc1cc(-c2cc3ccnc(NCc4cnc(-c5ccnc(C(F)(F)F)c5)c(F)c4)c3cn2)ccn1] |
| 31 | 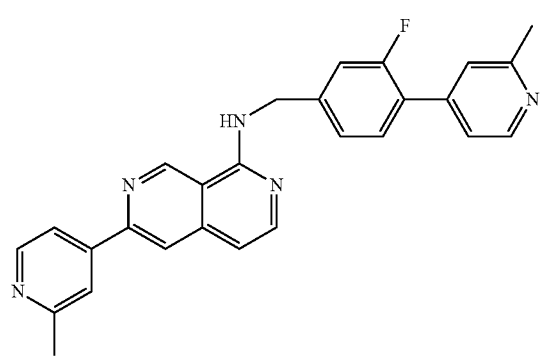 [SMILES: Cc1cc(-c2cc3ccnc(NCc4ccc(-c5ccnc(C)c5)c(F)c4)c3cn2)ccn1] |

TABLE 1-continued

| Compound | Structure |
|---|---|
| 32 | 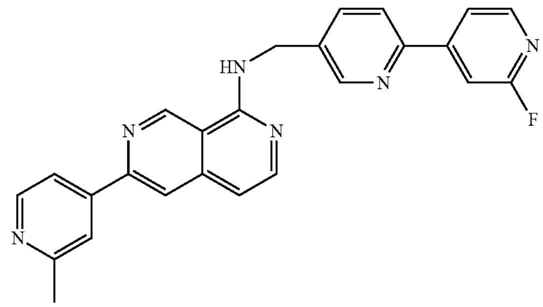 |
| 33 | 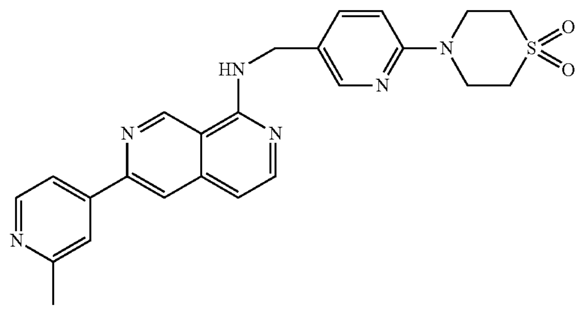 [SMILES: Cc1cc(-c2cc3ccnc(NCc4ccc(N5CCS(=O)(=O)CC5)nc4)c3cn2)ccn1] |
| 34 | 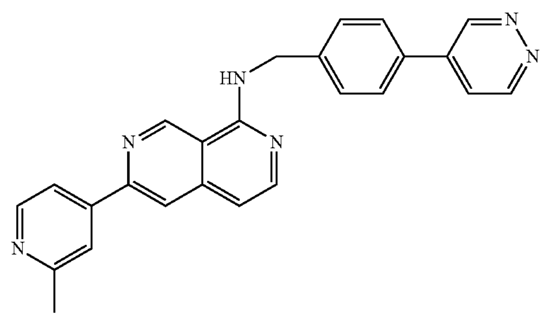 [SMILES: Cc1cc(-c2cc3ccnc(NCc4ccc(-c5ccnnc5)cc4)c3cn2)ccn1] |
| 35 | 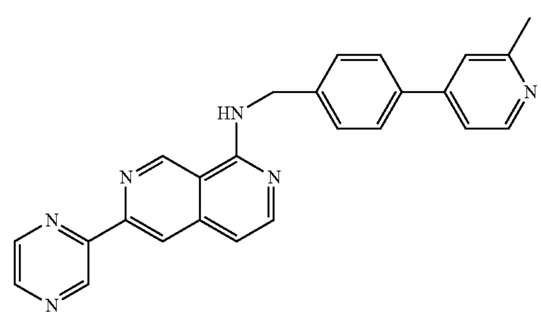 [SMILES: Cc1cc(-c2ccc(CNc3nccc4cc(-c5cnccn5)ncc34)cc2)ccn1] |
| 36 | 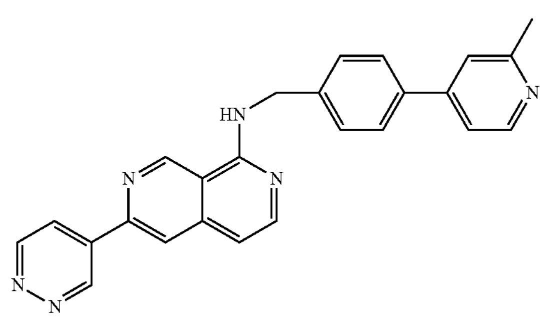 [SMILES: Cc1cc(-c2ccc(CNc3nccc4cc(-c5ccnnc5)ncc34)cc2)ccn1] |

TABLE 1-continued

| Compound | Structure |
|---|---|
| 37 | 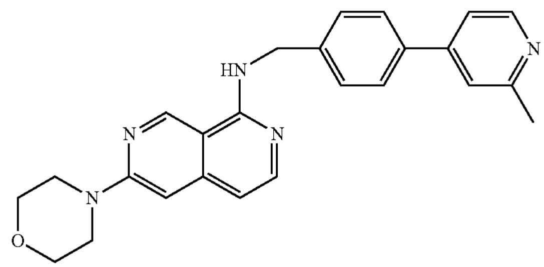 [SMILES: Cc1cc(-c2ccc(CNc3nccc4cc(N5CCOCC5)ncc34)cc2)ccn1] |
| 38 | 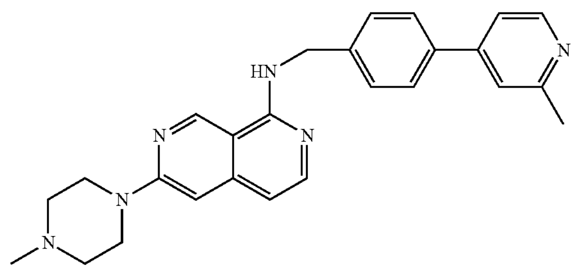 |
| 39 | 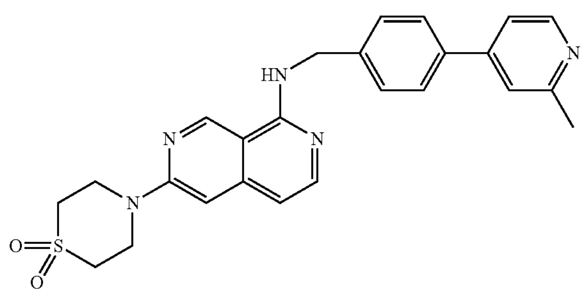 [SMILES: Cc1cc(-c2ccc(CNc3nccc4cc(N5CCS(=O)(=O)CC5)ncc34)cc2)ccn1] |
| 40 | 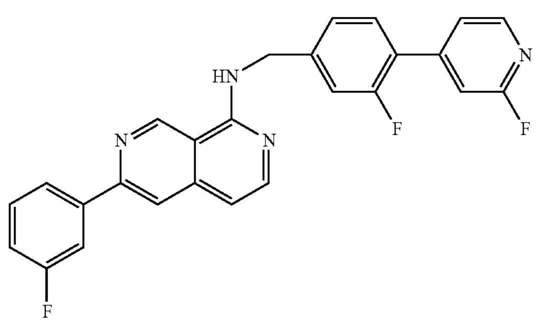 |
| 41 | 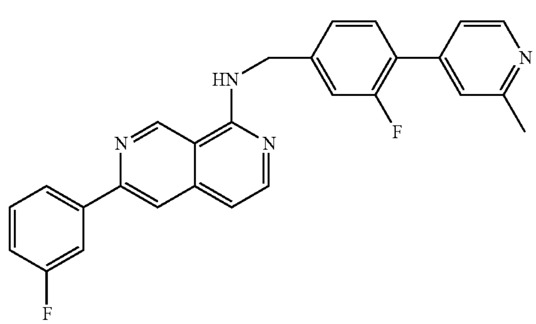 [SMILES: Cc1cc(-c2ccc(CNc3nccc4cc(-c5cccc(F)c5)ncc34)cc2F)ccn1] |

TABLE 1-continued

| Compound | Structure |
|---|---|
| 42 | 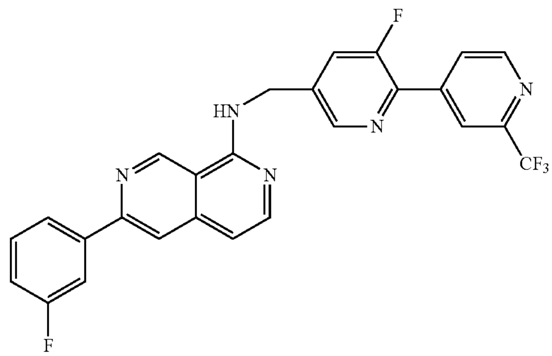 [SMILES: Fc1cccc(-c2cc3ccnc(NCc4cnc(-c5ccnc(C(F)(F)F)c5)c(F)c4)c3cn2)c1] |
| 43 | 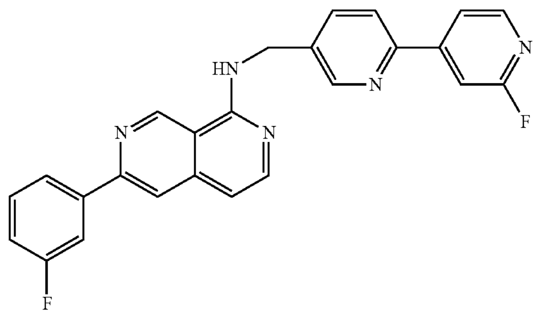 |
| 44 | 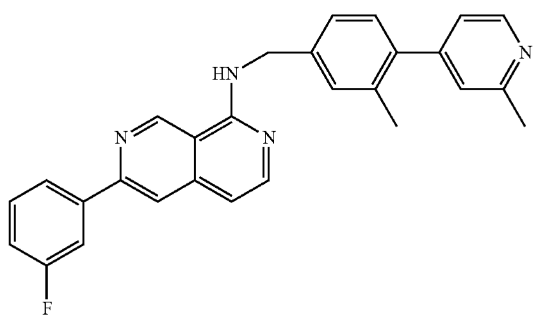 [SMILES: Cc1cc(-c2ccc(CNc3nccc4cc(-c5cccc(F)c5)ncc34)cc2C)ccn1] |
| 45 | 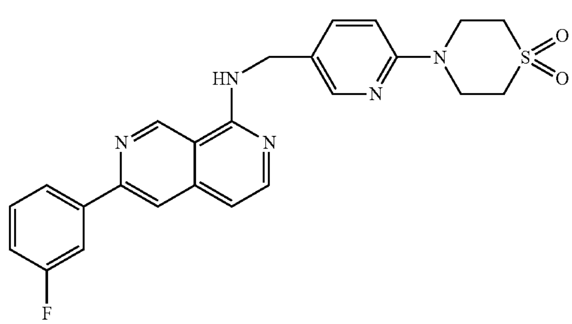 [SMILES: O=S1(=O)CCN(c2ccc(CNc3nccc4cc(-c5cccc(F)c5)ncc34)cn2)CC1] |

TABLE 1-continued

| Compound | Structure |
|---|---|
| 46 | 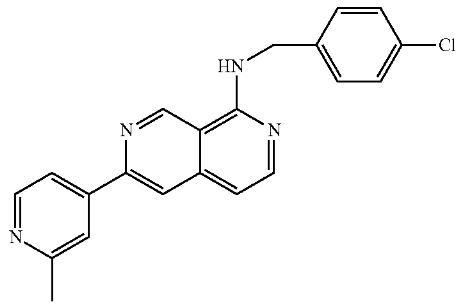 [SMILES: Cc1cc(-c2cc3ccnc(NCc4ccc(Cl)cc4)c3cn2)ccn1] |
| 47 | 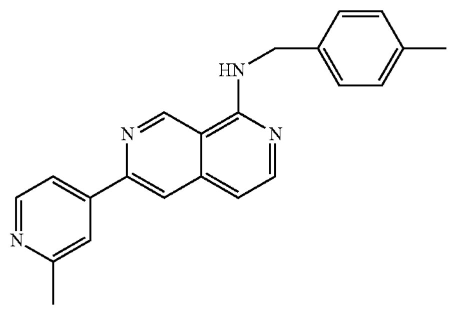 [SMILES: Cc1ccc(CNc2nccc3cc(-c4ccnc(C)c4)ncc23)cc1] |
| 48 | 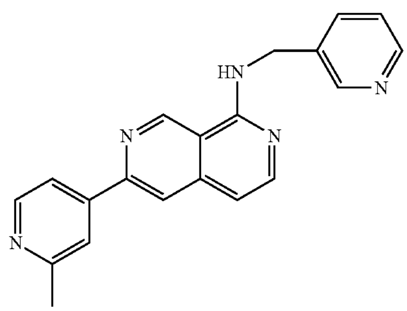 [SMILES: Cc1cc(-c2cc3ccnc(NCc4cccnc4)c3cn2)ccn1] |
| 49 | 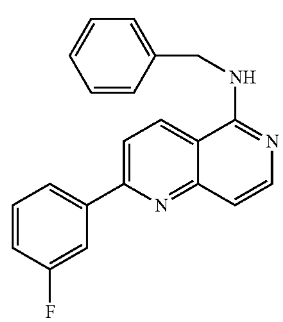 [SMILES: Fc1cccc(-c2ccc3c(NCc4ccccc4)nccc3n2)c1] |
| 50 | 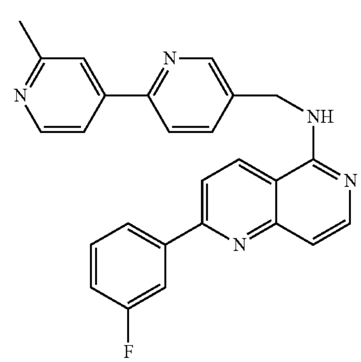 [SMILES: Cc1cc(-c2ccc(CNc3nccc4nc(-c5cccc(F)c5)ccc34)cn2)ccn1] |

TABLE 1-continued
| Compound | Structure |
|---|---|
| 51 | 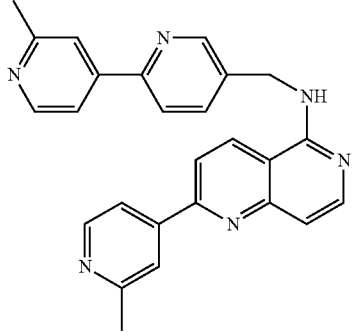 [SMILES: Cc1cc(-c2ccc(CNc3nccc4nc(-c5ccnc(C)c5)ccc34)cn2)ccn1] |
| 52 | 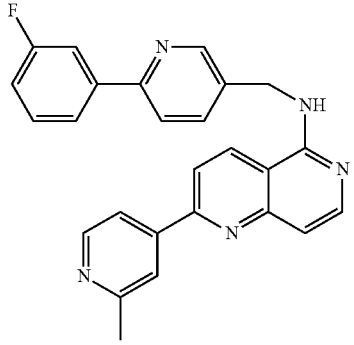 |
| 53 | 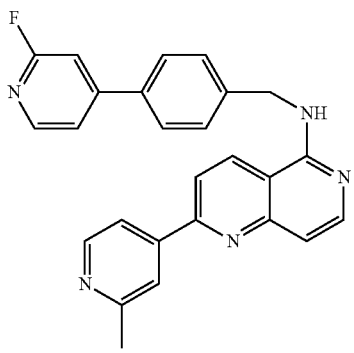 [SMILES: Cc1cc(-c2ccc3c(NCc4ccc(-c5cccc(F)c5)nc4)nccc3n2)ccn1] |
| 54 | 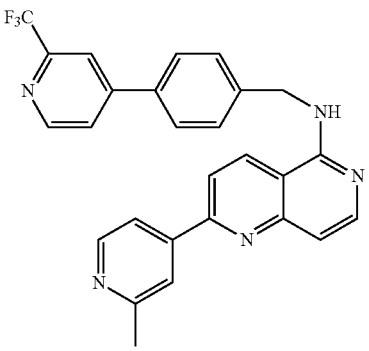 [SMILES: Cc1cc(-c2ccc3c(NCc4ccc(-c5ccnc(C(F)(F)F)c5)cc4)nccc3n2)ccn1] |

TABLE 1-continued
| Compound | Structure |
|---|---|
| 55 | 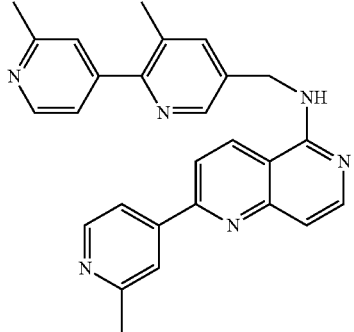 [SMILES: Cc1cc(-c2ccc3c(NCc4cnc(-c5ccnc(C)c5)c(C)c4)nccc3n2)ccn1] |
| 56 | 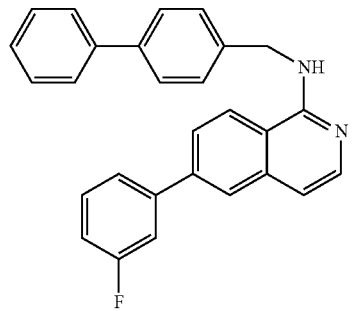 [SMILES: Fc1cccc(-c2ccc3c(NCc4ccc(-c5ccccc5)cc4)nccc3c2)c1] |
| 57 | 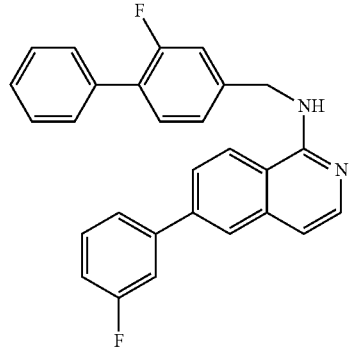 [SMILES: Fc1cccc(-c2ccc3c(NCc4ccc(-c5ccccc5)c(F)c4)nccc3c2)c1] |
| 58 | 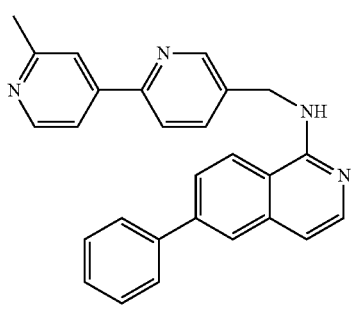 [SMILES: Cc1cc(-c2ccc(CNc3nccc4cc(-c5ccccc5)ccc34)cn2)ccn1] |

TABLE 1-continued

| Compound | Structure |
|---|---|
| 59 | 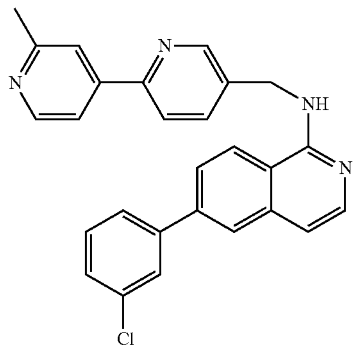 [SMILES: Cc1cc(-c2ccc(CNc3nccc4cc(-c5cccc(Cl)c5)ccc34)cn2)ccn1] |
| 60 | 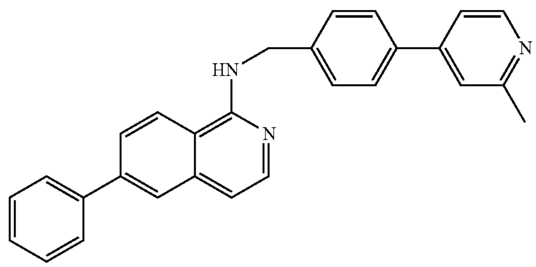 |
| 61 | 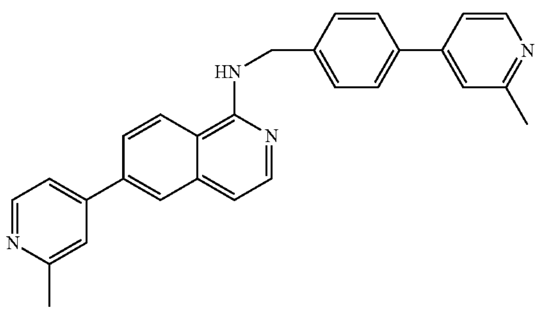 [SMILES: Cc1cc(-c2ccc(CNc3nccc4cc(-c5ccnc(C)c5)ccc34)cc2)ccn1] |
| 62 | 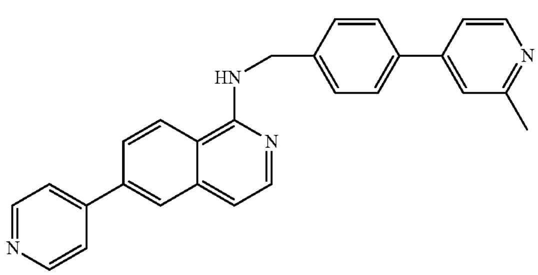 [SMILES: Cc1cc(-c2ccc(CNc3nccc4cc(-c5ccncc5)ccc34)cc2)ccn1] |
| 63 | 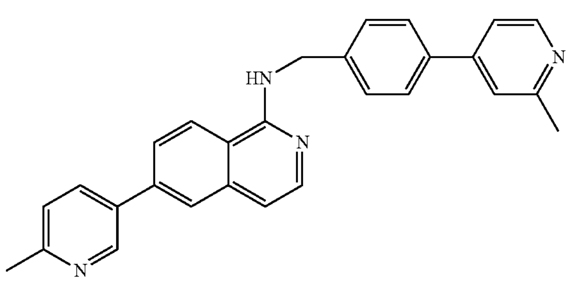 |

TABLE 1-continued
| Compound | Structure |
| --- | --- |
| 64 | 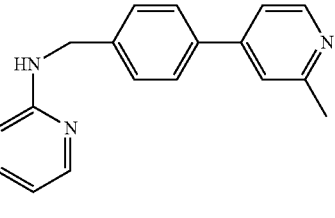 |
| 65 | 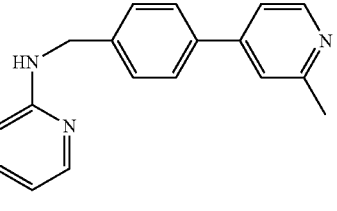 |
| 66 | 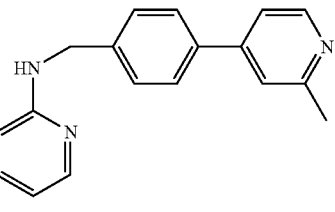 |
| 67 | 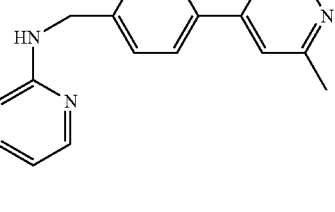 |
| 68 | 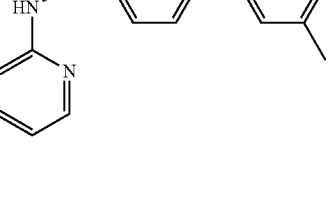 |

TABLE 1-continued
| Compound | Structure |
|---|---|
| 69 | 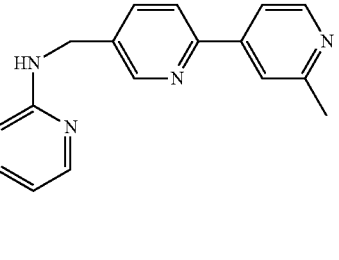 |
| 70 | 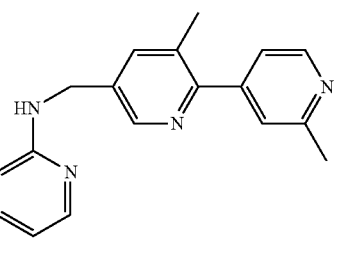 |
| 71 | 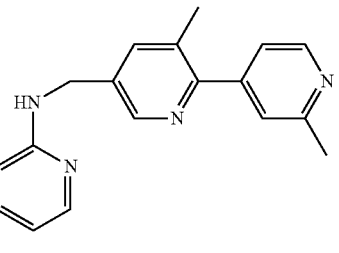 |
| 72 | 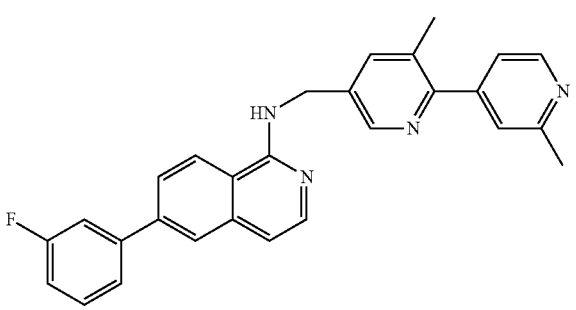 [SMILES: Cc1cc(-c2ncc(CNc3nccc4cc(-c5cccc(F)c5)ccc34)cc2C)ccn1] |
| 73 | 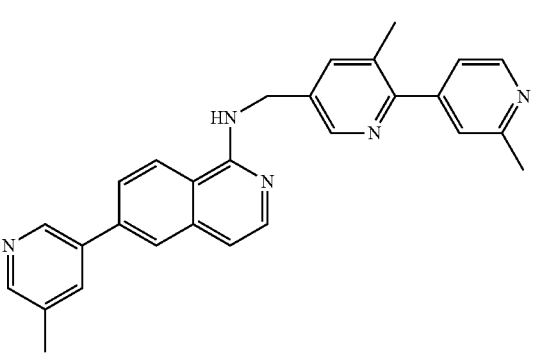 [SMILES: Cc1cncc(-c2ccc3c(NCc4cnc(-c5ccnc(C)c5)c(C)c4)nccc3c2)c1] |

TABLE 1-continued
| Compound | Structure |
|---|---|
| 74 | 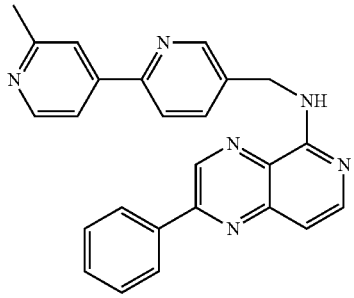 |
| 75 | 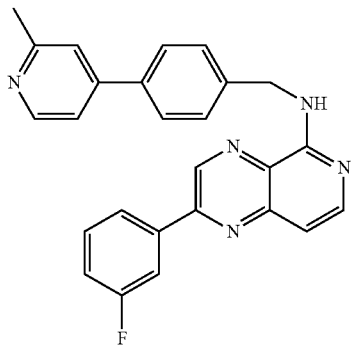 [SMILES: Cc1cc(-c2ccc(CNc3nccc4nc(-c5cccc(F)c5)cnc34)cn2)ccn1] |
| 76 | 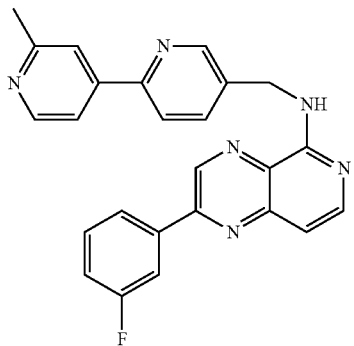 |
| 77 | 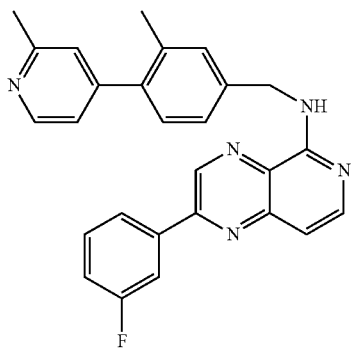 [SMILES: Cc1cc(-c2ccc(CNc3nccc4nc(-c5cccc(F)c5)cnc34)cc2C)ccn1] |

TABLE 1-continued

| Compound | Structure |
|---|---|
| 78 | 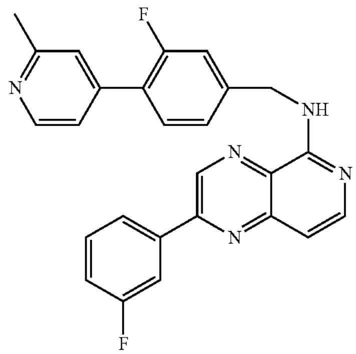 [SMILES: Cc1cc(-c2ccc(CNc3nccc4nc(-c5cccc(F)c5)cnc34)cc2F)ccn1] |
| 79 | 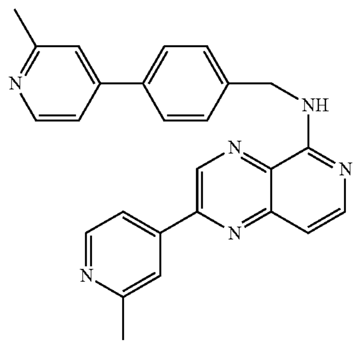 [SMILES: Cc1cc(-c2ccc(CNc3nccc4nc(-c5ccnc(C)c5)cnc34)cc2)ccn1] |
| 80 | 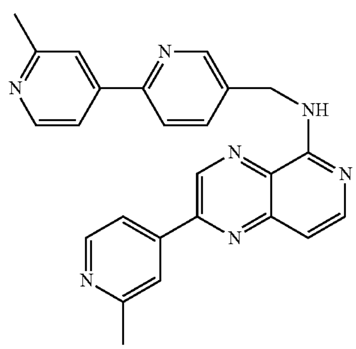 [SMILES: Cc1cc(-c2ccc(CNc3nccc4nc(-c5ccnc(C)c5)cnc34)cn2)ccn1] |
| 81 | 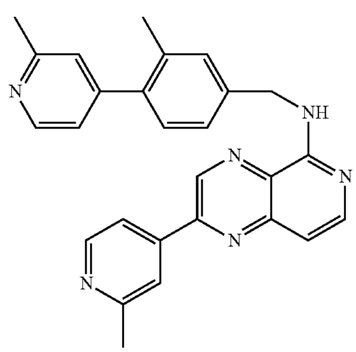 [SMILES: Cc1cc(-c2cnc3c(NCc4ccc(-c5ccnc(C)c5)c(C)c4)nccc3n2)ccn1] |

TABLE 1-continued
| Compound | Structure |
|---|---|
| 82 | 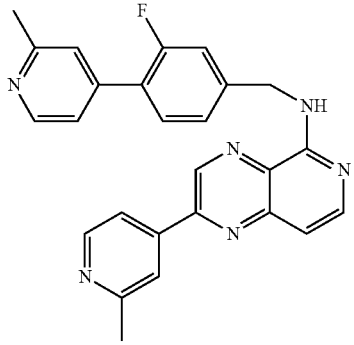 [SMILES: Cc1cc(-c2cnc3c(NCc4ccc(-c5ccnc(C)c5)c(F)c4)nccc3n2)ccn1] |
| 83 | 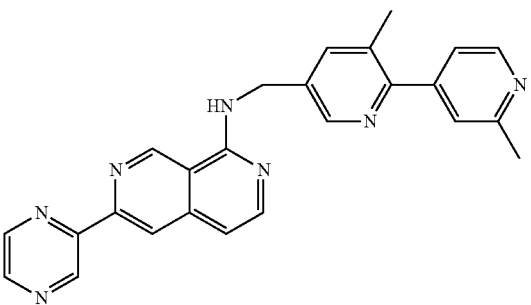 |
| 84 | 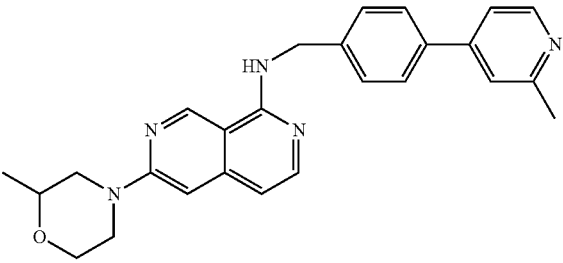 |
| 85 | 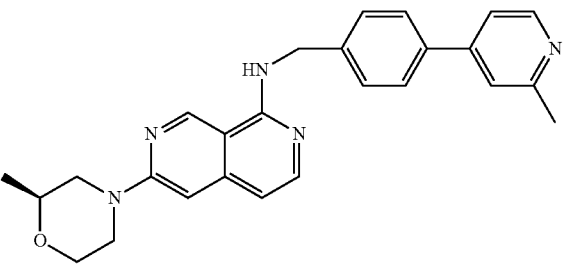 |
| 86 | 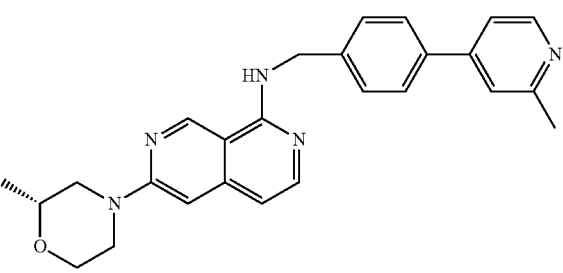 |

TABLE 1-continued

| Compound | Structure |
|---|---|
| 87 | 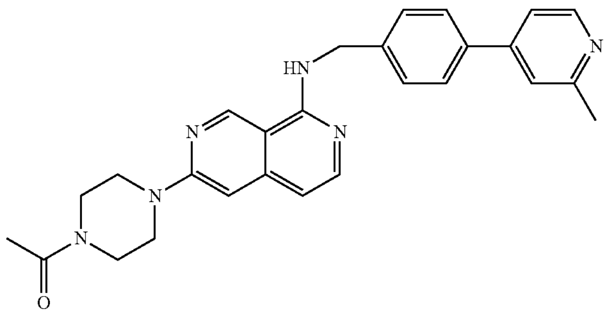 [SMILES: CC(=O)N1CCN(c2cc3ccnc(NCc4ccc(-c5ccnc(C)c5)cc4)c3cn2)CC1] |
| 88 | 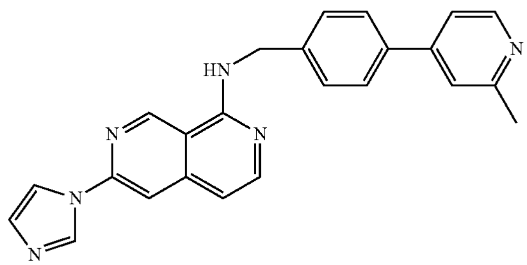 [SMILES: Cc1cc(-c2ccc(CNc3nccc4cc(-n5ccnc5)ncc34)cc2)ccn1] |
| 89 | 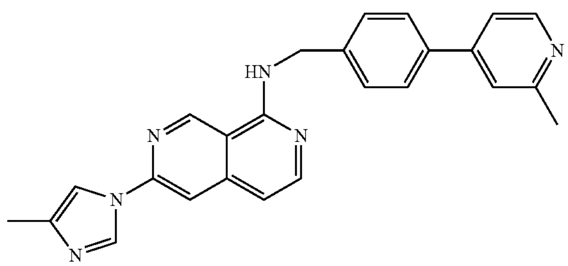 |
| 90 | 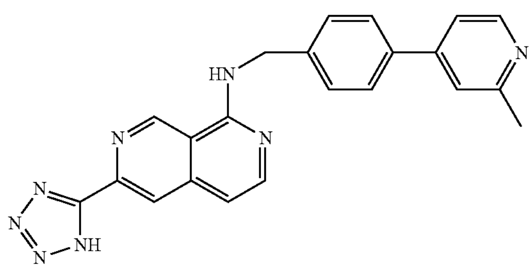 [SMILES: Cc1cc(-c2ccc(CNc3nccc4cc(-c5nnn[nH]5)ncc34)cc2)ccn1] |
| 91 | 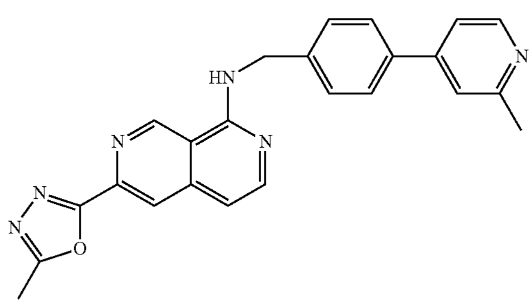 [SMILES: Cc1cc(-c2ccc(CNc3nccc4cc(-c5nnc(C)o5)ncc34)cc2)ccn1] |

TABLE 1-continued

| Compound | Structure |
|---|---|
| 92 | 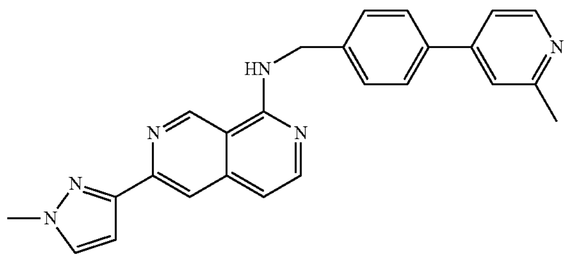 |
| 93 | 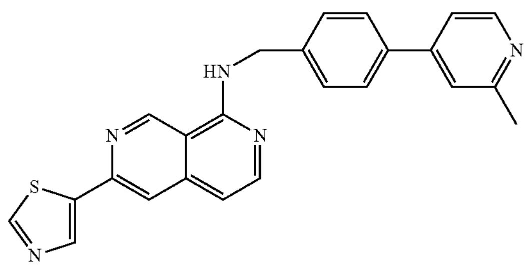 [SMILES: Cc1cc(-c2ccc(CNc3nccc4cc(-c5cnco5)ncc34)cc2)ccn1] |
| 94 | 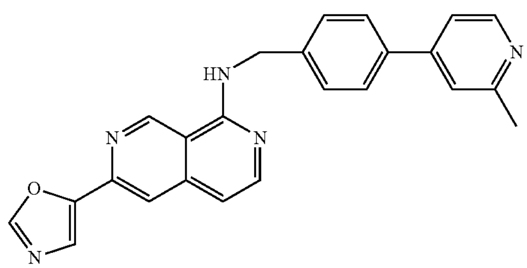 |
| 95 | 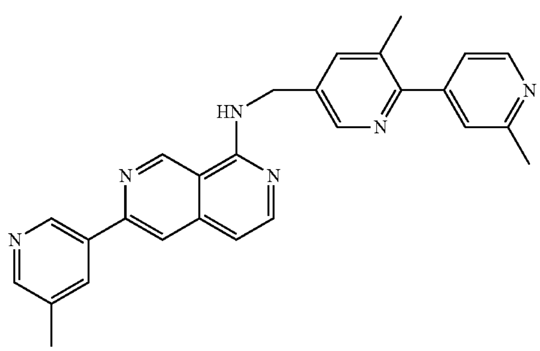 [SMILES: Cc1cncc(-c2cc3ccnc(NCc4cnc(-c5ccnc(C)c5)c(C)c4)c3cn2)c1] |
| 96 | 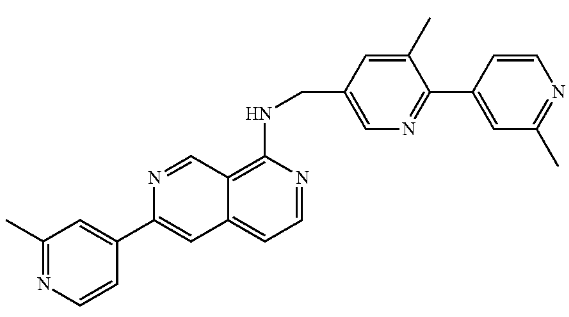 |

TABLE 1-continued

| Compound | Structure |
|---|---|
| 97 | 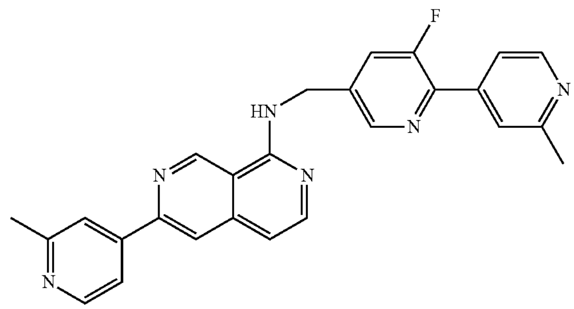 |
| 98 | 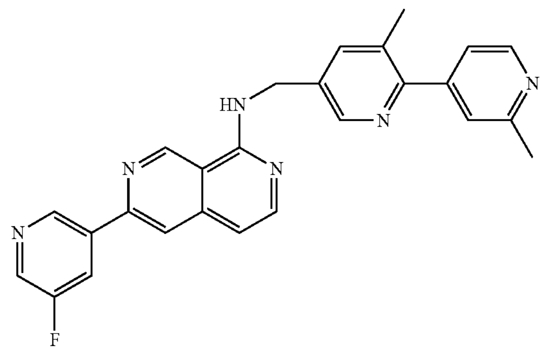 [SMILES: Cc1cc(-c2ncc(CNc3nccc4cc(-c5cncc(F)c5)ncc34)cc2C)ccn1] |
| 99 | 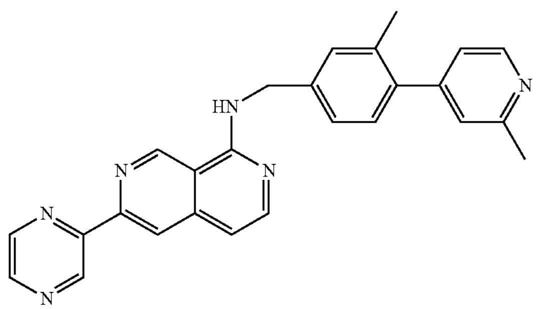 [SMILES: Cc1cc(-c2ccc(CNc3nccc4cc(-c5cnccn5)ncc34)cc2C)ccn1] |
| 100 | 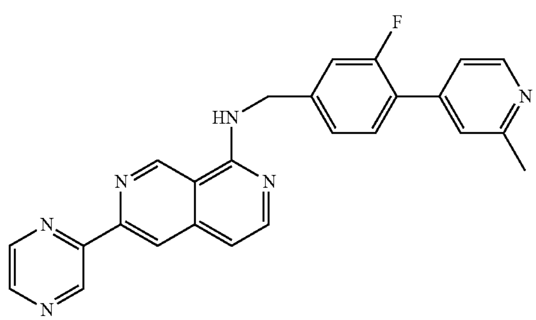 [SMILES: Cc1cc(-c2ccc(CNc3nccc4cc(-c5cnccn5)ncc34)cc2F)ccn1] |
| 101 | 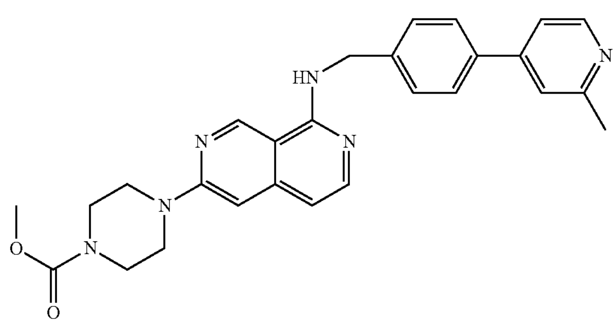 [SMILES: COC(=O)N1CCN(c2cc3ccnc(NCc4ccc(-c5ccnc(C)c5)cc4)c3cn2)CC1] |

TABLE 1-continued

| Compound | Structure |
|---|---|
| 102 | 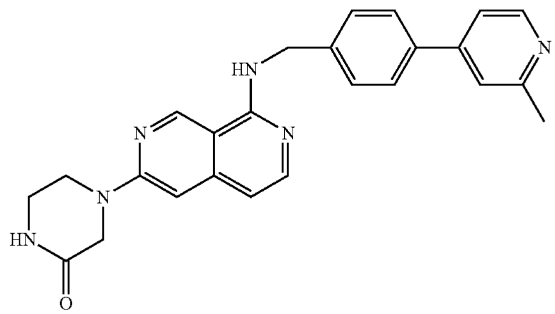 [SMILES: Cc1cc(-c2ccc(CNc3nccc4cc(N5CCNC(=O)C5)ncc34)cc2)ccn1] |
| 103 | 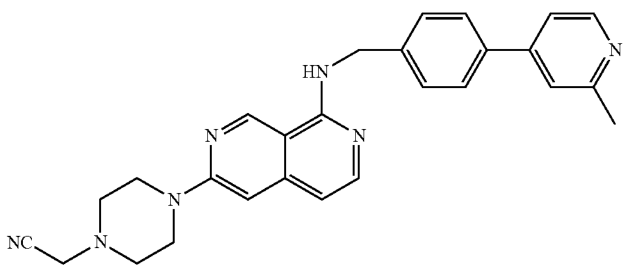 [SMILES: Cc1cc(-c2ccc(CNc3nccc4cc(N5CCN(CC#N)CC5)ncc34)cc2)ccn1] |
| 104 | 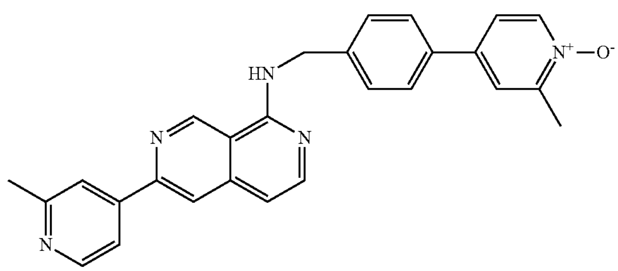 [SMILES: Cc1cc(-c2cc3ccnc(NCc4ccc(-c5cc[n+]([O-])c(C)c5)cc4)c3cn2)ccn1] |
| 105 | 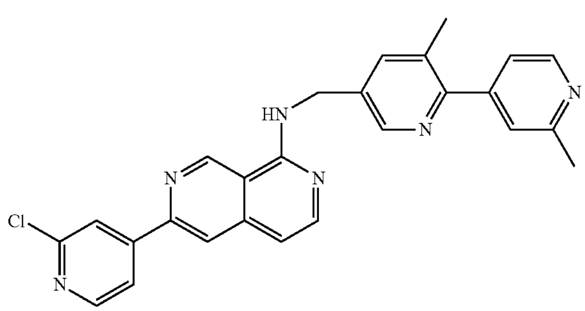 [SMILES: Cc1cc(-c2ncc(CNc3nccc4cc(-c5ccnc(Cl)c5)ncc34)cc2C)ccn1] |
| 106 | 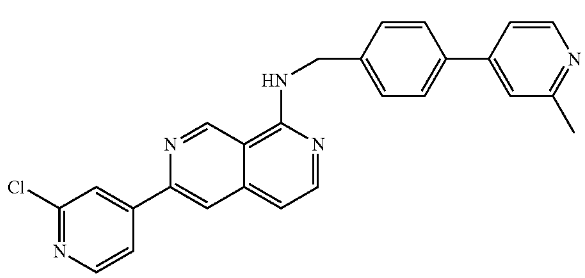 [SMILES: Cc1cc(-c2ccc(CNc3nccc4cc(-c5ccnc(Cl)c5)ncc34)cc2)ccn1] |

TABLE 1-continued

| Compound | Structure |
|---|---|
| 107 | 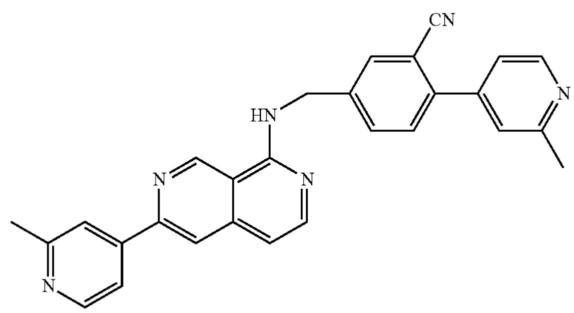 |
| 108 | 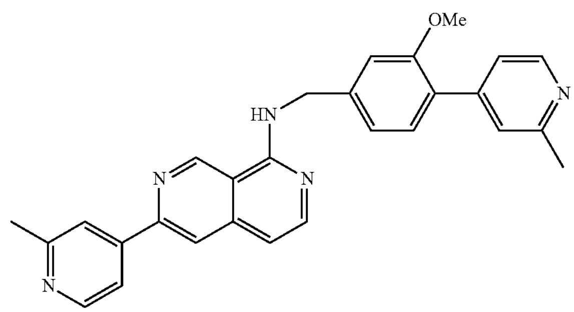 |
| 109 | 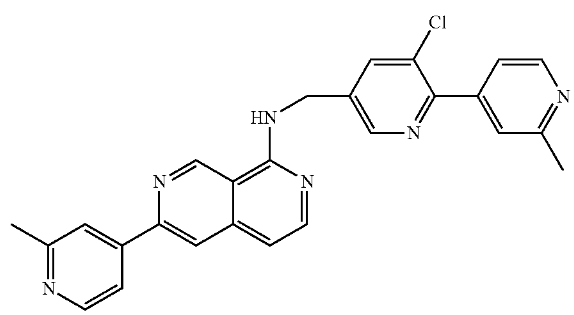 |
| 110 | 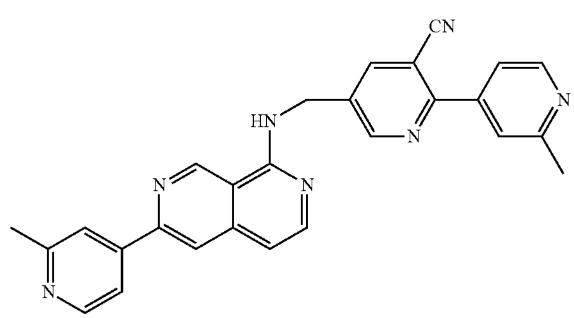 |
| 111 | 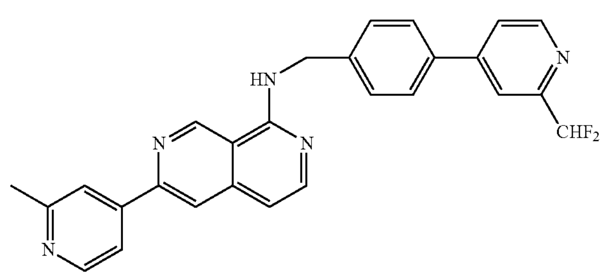 [SMILES: Cc1cc(-c2cc3ccnc(NCc4ccc(-c5ccnc(C(F)F)c5)cc4)c3cn2)ccn1] |

In some embodiments, the Wnt signal pathway inhibitor encapsulated within the liposome has a concentration between 0.5 mg/ml and 500 mg/ml, or 0.5 mg/ml and 50 mg/ml, or 0.5 mg/ml and 5 mg/ml, or 0.5 mg/ml and 1.5 mg/ml, or 0.6 mg/ml and 1.3 mg/ml.

In some embodiments, the molar ratio between the Wnt signal pathway inhibitor and the lipid molecules ranges from 1:5 to 1:50, or 1:5 to 1:20, or 1:10 to 1:20. In some embodiments the lipid molecules are selected from the group consisting of: soybean lecithin, hydrogenated soybean lecithin, distearoyl phosphatidylethanolamine-polyethylene glycol, and cholesterol. In one exemplary liposome formulation, the lipid molecules are hydrogenated soybean lecithin, cholesterol, and distearoyl phosphatidylethanolamine-polyethylene glycol. In some embodiments of this exemplary formulation the molar ratio among hydrogenated soybean lecithin, cholesterol, and distearoyl phosphatidylethanolamine-polyethylene glycol is 55:5:40. In some embodiments of this exemplary formulation the molar ratio between the Wnt signal pathway inhibitor and the sum amount of hydrogenated soybean lecithin, cholesterol, and distearoyl phosphatidylethanolamine-polyethylene glycol is 1:10.

In some embodiments, the liposome formulation as provided herein has an average particle size from 50 nm to 1000 nm, or from 50 nm to 200 nm.

In some embodiments, the liposome formulation as provided herein can be formulated as an oral formulation, or subcutaneous injection formulation, or intravenous injection formulation.

In another aspect, embodiments of the present invention provide to use of the liposome formulation as mentioned above in manufacturing a medicament for treating cancers.

BRIEF DESCRIPTION OF THE DRAWINGS

FIG. 3A shows result of HE staining upon treatment with oral formulation comprising Wnt signal pathway inhibitor. FIG. 3B shows result of HE staining upon treatment with liposome formulation comprising Wnt signal pathway inhibitor. FIG. 3C shows result of Alcian Blue staining upon treatment with oral formulation comprising Wnt signal pathway inhibitor. FIG. 3D shows result of Alcian Blue staining upon treatment with liposome formulation comprising Wnt signal pathway inhibitor.

DETAILED DESCRIPTION

Example 1

Figure 1:
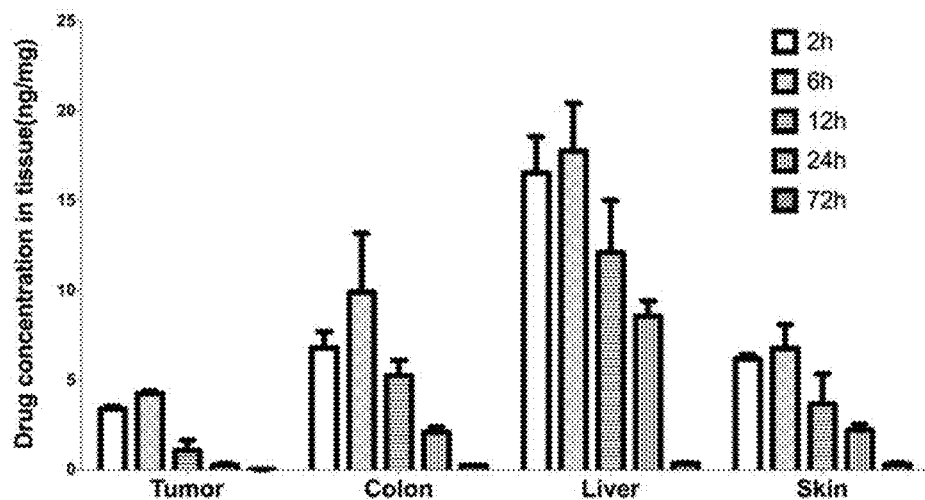
FIG. 1 shows distribution of the Wnt signal pathway inhibitor in tumor, liver, small intestine, skin at different time points upon administrating by intravenous injection.

Liposome Formulation for Delivery of Wnt Signal Pathway Inhibitor and the Method for Preparing the Same.

The present example illustrates the liposome formulation for delivery of a Wnt signal pathway inhibitor and the method for preparing the same, taking compound 28 as an example. The method for preparing the liposome formulation comprises:

(i) dissolving the Wnt signal pathway inhibitor and β-cyclodextrin in buffer solution of sodium dihydrogen phosphate (pH=5), vibrating overnight, removing supernatants by centrifugation to obtain saturated aqueous solution of Wnt signal pathway inhibitor comprising 30% β-cyclodextrin;

(ii) dissolving hydrogenated soybean lecithin, distearoyl phosphatidylethanolamine-polyethylene glycol and cholesterol in ethanol at a molar ratio of 55:5:40 to obtain ethanol solution of lipid molecules;

(iii) adding ammonium sulfate solution containing 30% β-cyclodextrin to ethanol solution of lipid molecules obtained in step (ii) to obtain blank vesicles, performing homogenization through a Millipore filtration membrane with pore size of 100 nm and 50 nm, and then performing dialysis using ammonium sulfate solution to remove ethanol from the blank vesicles and then performing dialysis using sodium dihydrogen phosphate to remove aqueous ammonium sulfate outside of the blank vesicles, thereby forming concentration gradient from interior to exterior of the blank vesicles; and (iv) preheating the blank vesicles obtained in step (iii) at 60° C. for 10 min by immersing them into the constant temperature vibrator, then adding saturated aqueous solution of Wnt signal pathway inhibitor comprising 30% β-cyclodextrin obtained in step (i) (molar ratio between the Wnt signal pathway inhibitor and the sum amount of hydrogenated soybean lecithin, cholesterol, and distearoyl phosphatidylethanolamine-polyethylene glycol is listed in below table), vibrating at constant temperature, after incubating for a certain period, performing dialysis using 10% saccharose solution to remove free drug, thereby obtaining liposome formulation with Wnt signal pathway inhibitor encapsulated therein (sample #1 and sample #2).

TABLE 2

Molar ratio between lipid molecules and Wnt signal pathway inhibitor for preparing the liposome formulation as mentioned above

| Sample | Molar ratio between the Wnt signal pathway inhibitor and the sum amount of hydrogenated soybean lecithin, cholesterol, and distearoyl phosphatidylethanolamine-polyethylene glycol (ratio of drug and lipid) |
|---|---|
| #1 | 1:10 |
| #2 | 1:20 |

Example 2

Measurement of Particle Size and Encapsulation Efficiency of the Liposome Formulation Measurement of particle size: The particle size of the liposome formulations as prepared according to Example 1 was determined by using a laser particle analyser (Malvern Corp.) according to light scattering principle. Parameters for measuring the particle size included: 25° C., viscosity of 0.089 cP, reflex angle of 1.33, angle of 90 degrees, balance for 60 seconds. The result was an average of 3 independent measurements.

The particle sizes of the samples as prepared according to Example 1 are listed in Table 3.

TABLE 3

Average particle size of liposome formulation as provided herein

| sample | Average particle size (nm) |
|---|---|
| #1 | 125 |
| #2 | 123 |

Measurement of Encapsulation Efficiency

During preparation of blank vesicles in Example 1, 100 ul sample of liposome formulation was obtained before performing dialysis for free drug and 100 ul sample of liposome formulation was obtained after performing dialysis for free drug. 900 ul methanol was added to the above two samples for demulsification and vibrated for 10 min at 37° C. on a constant temperature vibrator and then filtered by using 200 μm needle filters for HPLC detection.

Encapsulation Efficiency=Drug Concentration After Dialysis of Free Drug/Drug Concentration Before Dialysis of Free Drug The encapsulation efficiency and drug concentration in the final liposome formulation in samples #1 and #2 are listed in below Table 3.

TABLE 3

Encapsulation efficiency and drug concentration in the final liposome formulation of samples #1 and #2

| Sample | Encapsulation Efficiency | Final Drug Concentration mg/ml |
|---|---|---|
| #1 | 84% | 1.233 |
| #2 | 82% | 0.673 |

Example 3

Tissue Distribution and Efficiency of the Liposome Formulation in Mice Bearing Tumor Preparation of oral formulation comprising Wnt signal pathway inhibitor: 2 g Solutol 15 is thawed at 37° C. in a water bath and then sterilize water is added thereto, mixed at 37° C. in water bath, finally sterilize water is added thereto to final volume of 10 ml. 4 ml polyethylene glycol (PEG), 5 ml 20% Solutol 15 solution and 11 ml 5% glucose injectable solution are mixed together and are subjected to ultrasonic process, and filtered using 0.22 μm filtration membrane to remove bacteria, to prepare solvent for an oral formulation. 2 mg phosphate salt of a Wnt signal pathway inhibitor is dissolved in 20 ml solvent as prepared above and mixed and then subjected to ultrasonic process, thereby obtaining an oral formulation with a concentration of 1 mg/ml phosphate salt of Wnt signal pathway inhibitor.

Preparation of Liposome Formulation of Wnt Signal Pathway Inhibitor

Preparation of blank vesicles: 29.35 mg of hydrogenated soybean lecithin (HSPC), 9.82 mg of distearoyl phosphatidylethanolamine-polyethylene glycol (DSPE-PEG2000) and 10.83 mg of cholesterol were dissolved in 150 ul ethanol and heated up to 60° C. in a water bath, mixed using a magnetic stirrer till alcoholic solution of lipid molecules was formed. 805 μl of ammonium sulfate solution containing 30% β-cyclodextrin by mass (200 mmol, pH=4.0) is gently added to the alcoholic solution of lipid molecules. The resultant blank vesicles were homogenized by passing through filtration membrane with pore size of 100 nm and 50 nm to obtain blank vesicles with particle size of 90 nm. Dialysis was performed against ammonium sulfate solution (200 mmol, pH=4.0, 2 L) for 3 times at 4° C., each for 4-6 hours, to remove ethanol from the blank vesicles. Dialysis was performed again against a buffer solution of sodium dihydrogen phosphate (200 mmol, pH=5.0, 2 L) for 3 times at 4° C., each for 4-6 hours, to remove aqueous phase of ammonium sulfate outside of the blank vesicles till concentration gradient of ammonium sulfate from interior to exterior of the blank vesicles is formed. The resultant blank vesicles have a lipid concentration of 50 mg/ml and molar ration HSPC:DSPE-PEG2000:CHOL of 55:5:40.

Preparation of saturated aqueous solution of a Wnt signal pathway inhibitor: 20 mg of the Wnt signal pathway inhibitor and 0.3 g β-cyclodextrin are dissolved in buffer solution of sodium dihydrogen phosphate (200 mmol, pH=5.0, 1 ml) and vibrated overnight. Supernatant is removed by centrifugation to obtain saturated aqueous solution of Wnt signal pathway inhibitor containing 30% β-cyclodextrin (solubility is about 2.5 mg/ml).

Preparation of a liposome-encapsulated formulation of a Wnt signal pathway inhibitor: 500 μl of blank vesicles are preheated at 60° C. for 10 min on a constant temperature vibrator, to which 730 μl of a preheated saturated aqueous solution of the Wnt signal pathway inhibitor at 60° C. is added. The mixture was vibrated under constant temperature for 40 min at 750 rpm. Dialysis was performed against 10% saccharose solution (1 L) for 3 times at 4° C., each for 4-6 hours, to remove free drug. The liposome formulation with the Wnt signal pathway inhibitor at 1.02 mg/ml encapsulated therein was obtained.

Distribution in Tissues In Vivo

18 SPF nude mice inoculated with GA67 were grouped into 6 groups (n=3). The liposome formulations with drug concentration of 1 mg/ml were administrated to mice via tail vein injection. 10 mg/kg drug was administrated for each group. Mice were sacrificed at 2, 6, 12, 24, 72 h after administration. Tumor, liver, intestine and skin were removed out, washed with PBS for 10 seconds, dried with filter paper and then weighed. Each tissue was cut into pieces in a homogenation tube and diluted with PBS at a ratio of 50 mg tissue vs. 250 μl PBS. 2-3 glass beads are added to each homogenation tube and tissues were homogenized by using a tissue grinder (liver for 5 min, intestine for 5 min, tumor for 10 min, skin for 15 min) for further use. Tissue homogenation solution and methanol (1:4 v/v) were added to 1.5 ml centrifugation tubes for mixing to precipitate protein. Centrifugation was performed at 14000 rpm at 4° C. for 10 min and the supernatant was removed for further use. 100 μl supernatant was added to 1.5 ml centrifugation tubes and 900 μl methanol was added thereto, a 10-fold dilution, and mixed. 900 μl methanol was added to 100 μl of the methanol-diluted supernatant, a 100-fold dilution, for determination of final drug concentration.

In Vivo Efficiency

18 SPF nude mice inoculated with GA67 were grouped to 6 groups (n=3). The liposome formulation of the Wnt signal pathway inhibitor was administrated to mice via tail vein injection and the oral formulation of the Wnt signal pathway inhibitor was administrated to mice through gavage. Administration regimens for each group are shown below:

The first group (Control group): administration of blank liposome formulation via tail vein q.a.d. for 7 times;

The second group (10 mg/kg PO qod): administration of the oral formulation of the Wnt signal pathway inhibitor via gavage at a dose of 10 mg/kg q.a.d. for 7 times;

The third group (5 mg/kg PO qd): administration of the oral formulation of the Wnt signal pathway inhibitor via gavage at a dose of 5 mg/kg per day for 14 times;

The fourth group (1 mg/kg IV): administration of the liposome formulation of the Wnt signal pathway inhibitor via tail vein at a dose of 1 mg/kg q.a.d. for 7 times;

The fifth group (3 mg/kg IV): administration of the liposome formulation of the Wnt signal pathway inhibitor via tail vein at a dose of 3 mg/kg q.a.d. for 7 times;

The sixth group (10 mg/kg IV): administration of the liposome formulation of the Wnt signal pathway inhibitor via tail vein at a dose of 10 mg/kg q.a.d. for 7 times.

On days 0, 4, 6, 9, 13, and 16 upon first administration, tumor volume was measured by a calliper (tumor volume=$0.5a \times b^2$), wherein a is long diameter of the tumor and b is short diameter of the tumor. Statistical comparisons among tumor volumes of respective groups were performed using Student's t-Test. Data was analysed by using SPSS 18.0. $P<0.05$ represents significant difference.

On day 2 after final administration, the second group mice and the sixth group mice were sacrificed and tumor tissues were removed and subjected to HE staining and Alcine Blue staining as described below.

HE Staining (1) Deparaffinization and Rehydration: deparaffinization of paraffin section with dimethylbenzene for 10 min, re-deparaffinization with dimethylbenzene for 5 min and then immersing into anhydrous alcohol, 95% alcohol, 90% alcohol, 80% alcohol, 70% alcohol for 3-5 min each, finally immersing into distilled water for 3 min;
(2) Staining: placing paraffin section into hematoxylin to stain for 10-30 min;
(3) Water Washing: washing with water to make the section become blue in color;
(4) Hydration: placing the section into ethanol solution with 1% hydrochloric acid to fade for 5 s;
(5) Rinsing: washing the section with water again to restore blue color;
(6) Dehydration: placing the section into 70% ethanol to dehydrate for 30 s and 80% ethanol to dehydrate for 2 min;
(7) Re-staining: performing contrast staining with ethanol solution containing 0.5% eosin for 2 min;
(8) Re-dehydration: placing the section into 95% ethanol for rinsing and then immersing into anhydrous alcohol for 4 min;
(9) Transparentizing: immersing the section into dimethylbenzene for 3 min and then re-immersing for 3 min;
(10) Mounting: mounting with neutral resin.

Alcine Blue Staining (1) performing deparaffinization and rehydration as described above, and then washing with 1×PBS 3 times, each for 2 min;
(2) placing the paraffin section into Alcine blue solution to stain for 20 min and then rinsing with 3% acetic acid solution for 2 min and then washing with 1×PBS 3 times, each for 2 min;
(3) re-staining with hematoxylin;
(4) dehydrating with ethanol under gradient concentration and then observing under microscope.

FIG. 1 shows the distribution of the liposome formulation of the Wnt signal pathway inhibitor in tumor, liver, intestine and skin at different time points following intravenous injection. As shown in FIG. 1, drug concentration in respective tissues reaches maximum value at 6 h and then is gradually reduced. At 72 h, little drug is detected in respective tissues. The drug concentration in the tumor was sufficient to meet treatment requirements. Importantly, re-distribution and re-accumulation of Wnt signal pathway inhibitor in skin and intestine are not found in the results of tissue distribution of the Wnt signal pathway inhibitor. This indicates that side effects of the drug should be reduced by using a liposome formulation of Wnt signal pathway inhibitors and that the drug was targeted to the tumor site.

Figure 2:
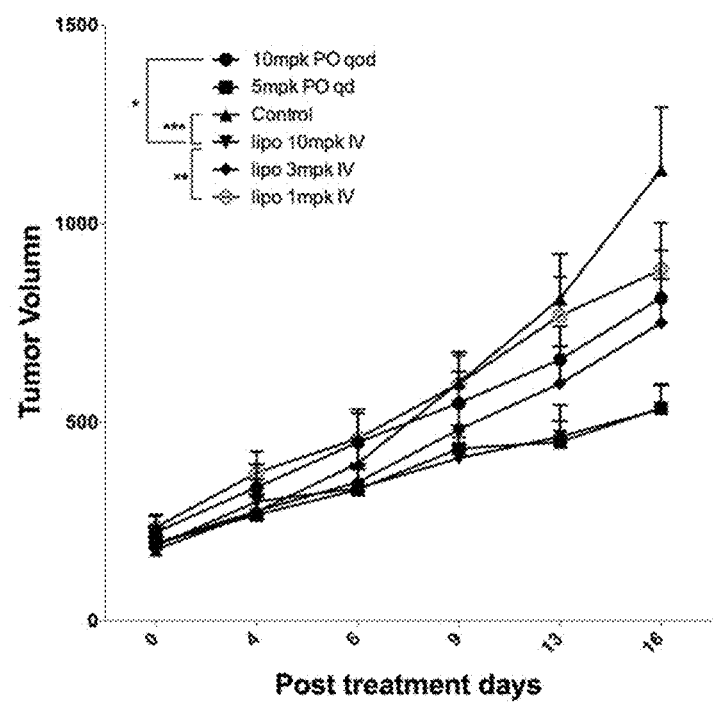
FIG. 2 shows variation of tumor volume upon administration of various formulations.

FIG. 2 shows change of tumor volume upon administration of the various formulations. As shown in FIG. 2, upon treating each group for 16 days, in comparison with blank control group, the group administrated the 10 mg/kg of the liposome formulation of the Wnt signal pathway inhibitor showed superior anti-tumor effect and exhibited anti-gastric cancer effect with statistical significance ($P<0.001$). The group administered 10 mg/kg of the liposome formulation of the Wnt signal pathway inhibitor had superior anti-tumor effect to the group administrated the 10 mg/kg oral formulation, which exhibit statistical difference ($P<0.05$). This indicates that the liposome formulation was able to effectively deliver the drug to the tumor tissue, so as to enhance anti-tumor effect as compared to the oral formulation. The anti-tumor effect of the liposome formulation of Wnt signal pathway inhibitor increased as the concentration of drug was increased. The anti-tumor effect of the groups administrated the 10 mg/kg formulations was remarkably superior to the groups administrated the 1 mg/kg formulations and exhibited statistical difference ($P<0.01$).

Figure 3:
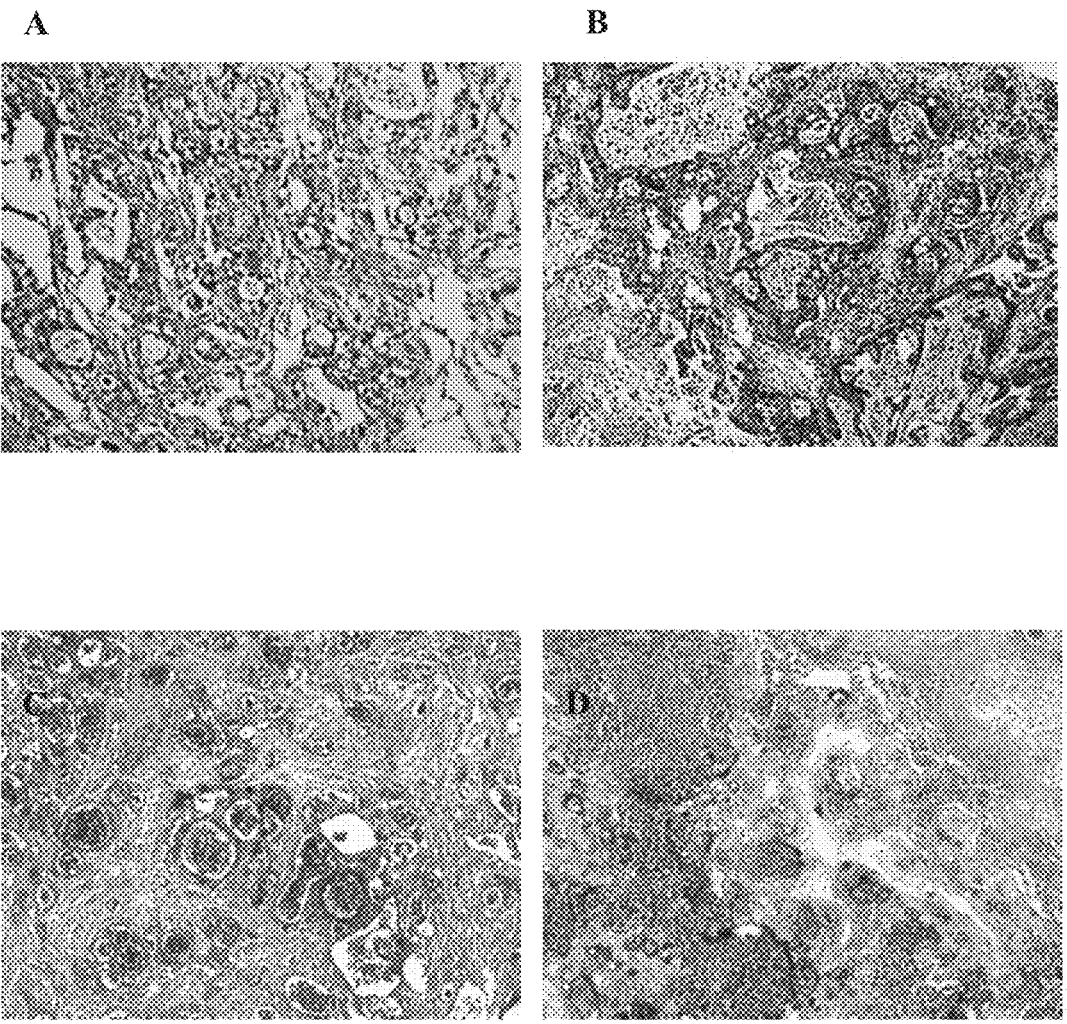
FIG. 3 shows results of HE staining and Alcian Blue staining upon treatment with various formulations comprising Wnt signal pathway inhibitor.

FIGS. 3A to 3D are HE and Alcine Blue staining results following treatment with various liposome formulations of the Wnt signal pathway inhibitor. As shown in FIGS. 3A and 3B, the HE staining results indicate that the tumor tissues after being treated with the liposome formulation of the Wnt signal pathway inhibitor showed high differentiation and are in loose status with a lot of pores. As shown in FIGS. 3C and 3D, the Alcine Blue staining results showed blue signal, representing more differentiation. This indicates that the Wnt signal pathway inhibitor inhibited growth of tumor through differentiation and apoptosis of tumor cells and that the tumor treated with the liposome formulation of the Wnt signal pathway inhibitor exhibited a higher degree of differentiation than tumor treated with the oral formulation.

Conclusion

The liposome formulation as provided herein encapsulates Wnt signal pathway inhibitors at a concentration higher than the therapeutically effective concentration. The concentration of the Wnt signal pathway inhibitor encapsulated in the liposome formulation as provided herein is enhanced and the toxicity of Wnt signal pathway inhibitor is reduced. The Wnt signal pathway inhibitors can be effectively delivered to tumor tissue via the liposome formulation, so as to enhance anti-tumor effect. The tumor treated with the liposome formulation as provided herein exhibits a higher degree of differentiation than the tumor treated with the oral formulation, which indicates that the liposome formulation as provided herein can more effectively inhibit growth of tumor than the oral formulation.

What we claimed is:

1. A liposome formulation for delivery of a Wnt signal pathway inhibitor, comprising lipid molecules encapsulating the Wnt signal pathway inhibitor,
   wherein:
      the Wnt signal pathway inhibitor encapsulated within the liposome formulation has a concentration between 0.6 mg/ml and 1.3 mg/ml;
      the Wnt signal pathway inhibitor is compound 28, having the structure

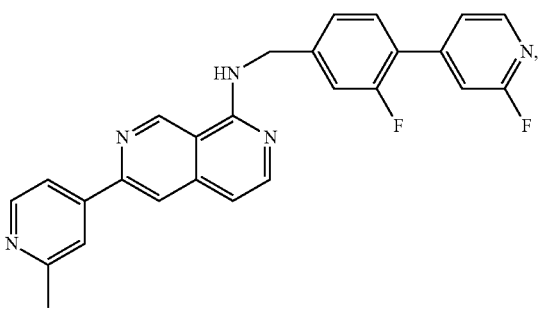 [SMILES: Cc1cc(-c2cc3ccnc(NCc4ccc(-c5ccnc(F)c5)c(F)c4)c3cn2)ccn1]

or a pharmaceutically acceptable salt thereof;
the lipid molecules are hydrogenated soybean lecithin, cholesterol, and distearoyl phosphatidylethanolamine-polyethylene glycol, and the molar ratio among hydrogenated soybean lecithin, cholesterol, and distearoyl phosphatidylethanolamine-polyethylene glycol is 55:5:40, and the molar ratio between the Wnt signal pathway inhibitor and the sum amount of hydrogenated soybean lecithin, cholesterol, and distearoyl phosphatidylethanolamine-polyethylene glycol is 1:10; and wherein:
the liposome formulation is prepared through following steps:
(i) dissolving the Wnt signal pathway inhibitor and β-cyclodextrin as a solubilizing agent in buffer solution of sodium dihydrogen phosphate at pH=5, vibrating overnight, removing supernatants by centrifugation to obtain saturated aqueous solution of the Wnt signal pathway inhibitor comprising 30% β-cyclodextrin;
(ii) dissolving hydrogenated soybean lecithin, distearoyl phosphatidylethanolamine-polyethylene glycol and cholesterol in ethanol at a molar ratio of 55:5:40 to obtain ethanol solution of lipid molecules;
(iii) adding ammonium sulfate solution containing 30% β-cyclodextrin to the ethanol solution of lipid molecules obtained in step (ii) to obtain blank vesicles, performing homogenization through MILLIPORE filtration membranes with pore sizes of 100 nm and 50 nm, and then performing dialysis using ammonium sulfate solution to remove ethanol from the blank vesicles and then performing dialysis using sodium dihydrogen phosphate to remove aqueous ammonium sulfate outside of the blank vesicles, thereby forming concentration gradient from interior to exterior of the blank vesicles;
(iv) preheating the blank vesicles obtained in step (iii) at 60° C. for 10 min by immersing them into the constant temperature vibrator, then adding saturated aqueous solution of Wnt signal pathway inhibitor comprising 30% β-cyclodextrin obtained in step (i), vibrating at constant temperature, after incubating for a certain period, performing dialysis using 10% saccharose solution to remove free drug, thereby obtaining the liposome formulation with Wnt signal pathway inhibitor encapsulated therein.

2. The liposome formulation of claim 1, wherein the liposome formulation has an average particle size from 50 nm to 1000 nm.

3. The liposome formulation of claim 2, wherein the liposome formulation has an average particle size from 50 nm to 200 nm.

4. The liposome formulation of claim 1, wherein the liposome formulation is formulated as an oral formulation, or a subcutaneous injection formulation, or an intravenous injection formulation.

5. The liposome formulation of claim 2, wherein the liposome formulation is formulated as an oral formulation, or a subcutaneous injection formulation, or an intravenous injection formulation.

6. The liposome formulation of claim 3, wherein the liposome formulation is formulated as an oral formulation, or a subcutaneous injection formulation, or an intravenous injection formulation.

7. A method of treating cancer, comprising administration of the liposome formulation of claim 1 to a subject in need thereof.

* * * * *